(12) United States Patent
Kale et al.

(10) Patent No.: US 11,726,784 B2
(45) Date of Patent: Aug. 15, 2023

(54) PATIENT MONITORING USING EDGE SERVERS HAVING DEEP LEARNING ACCELERATOR AND RANDOM ACCESS MEMORY

(71) Applicant: Micron Technology, Inc., Boise, ID (US)

(72) Inventors: Poorna Kale, Folsom, CA (US); Jaime Cummins, Bainbridge Island, WA (US)

(73) Assignee: Micron Technology, Inc., Boise, ID (US)

( * ) Notice: Subject to any disclaimer, the term of this patent is extended or adjusted under 35 U.S.C. 154(b) by 312 days.

(21) Appl. No.: 16/845,010

(22) Filed: Apr. 9, 2020

(65) Prior Publication Data
US 2021/0318871 A1    Oct. 14, 2021

(51) Int. Cl.
*G06F 9/30*    (2018.01)
*G06F 9/50*    (2006.01)
(Continued)

(52) U.S. Cl.
CPC ........ *G06F 9/30007* (2013.01); *A61B 5/0022* (2013.01); *A61B 5/7275* (2013.01); *A61B 5/746* (2013.01); *G06F 9/3893* (2013.01); *G06F 9/5027* (2013.01); *G06N 3/063* (2013.01); *H04L 67/10* (2013.01)

(58) Field of Classification Search
CPC ................................ A61B 5/0022; G06N 3/08
See application file for complete search history.

(56) References Cited

U.S. PATENT DOCUMENTS

| 5,815,458 A | 9/1998 | Chevallier et al. |
| 7,873,812 B1 | 1/2011 | Mimar |
| (Continued) | | |

FOREIGN PATENT DOCUMENTS

| WO | 2005091203 | 9/2005 |
| WO | 2020058560 | 3/2020 |

OTHER PUBLICATIONS

Title: Integrated Circuit Device with Deep Learning Accelerator and Random Access Memory, U.S. Appl. No. 16/844,988, filed Apr. 9, 2020 Inventors: Poorna Kale et al. Status: Docketed New case—Ready for Examination Status Date: Aug. 20, 2021.

(Continued)

*Primary Examiner* — Fabricio R Murillo Garcia
(74) *Attorney, Agent, or Firm* — Greenberg Traurig

(57) ABSTRACT

Systems, devices, and methods related to a Deep Learning Accelerator and memory are described. An edge server may be configured on a local area network to receive sensor data of a person, such as a patient in a hospital or care center. The edge server may be implemented using an integrated circuit device having: a Deep Learning Accelerator configured to execute instructions with matrix operands; and random access memory configured to store first instructions of an Artificial Neural Network executable by the Deep Learning Accelerator and second instructions of a server application executable by a Central Processing Unit. An output of the Artificial Neural Network with the sensor data as input may identify a condition of the person, based on which the server application generates an alert, causing a central server to request intervention of the detected or predicted condition for the person.

18 Claims, 12 Drawing Sheets

(51) Int. Cl.
  *G06F 9/38* (2018.01)
  *H04L 67/10* (2022.01)
  *A61B 5/00* (2006.01)
  *G06N 3/063* (2023.01)

(56) References Cited

U.S. PATENT DOCUMENTS

| | | | |
|---|---|---|---|
| 10,387,122 | B1 | 8/2019 | Olsen |
| 10,515,135 | B1 | 12/2019 | Zejda et al. |
| 10,678,479 | B1 | 6/2020 | Diamant et al. |
| 10,722,210 | B2 | 7/2020 | Yu |
| 10,754,764 | B2 | 8/2020 | Lekivetz et al. |
| 10,885,314 | B2 | 1/2021 | Liu |
| 10,978,382 | B2 | 4/2021 | Lai et al. |
| 11,204,747 | B1 | 12/2021 | Zejda et al. |
| 11,355,175 | B2 | 6/2022 | Kale et al. |
| 11,461,651 | B2 | 10/2022 | Kale et al. |
| 11,544,548 | B2 | 1/2023 | Bae |
| 2006/0230213 | A1 | 10/2006 | Tousek et al. |
| 2010/0076915 | A1 | 3/2010 | Xu et al. |
| 2011/0307228 | A1* | 12/2011 | Kasabov ............ G06Q 10/04 703/2 |
| 2012/0257742 | A1 | 10/2012 | Ebeid et al. |
| 2014/0279746 | A1 | 9/2014 | De Bruin et al. |
| 2015/0038806 | A1* | 2/2015 | Kaleal, III ........... A61B 5/4833 600/301 |
| 2017/0316312 | A1 | 11/2017 | Goyal et al. |
| 2018/0307974 | A1 | 10/2018 | Fang et al. |
| 2018/0307976 | A1 | 10/2018 | Fang et al. |
| 2019/0027018 | A1 | 1/2019 | Corpus et al. |
| 2019/0042411 | A1 | 2/2019 | Muralimanohar et al. |
| 2019/0046039 | A1 | 2/2019 | Ramesh et al. |
| 2019/0050733 | A1 | 2/2019 | Bopardikar et al. |
| 2019/0121837 | A1 | 4/2019 | Azizi et al. |
| 2019/0164279 | A1 | 5/2019 | Ionasec |
| 2019/0171941 | A1 | 6/2019 | Quach et al. |
| 2019/0180170 | A1 | 6/2019 | Huang et al. |
| 2019/0188587 | A1 | 6/2019 | Gupta et al. |
| 2019/0258306 | A1 | 8/2019 | Croxford |
| 2019/0286972 | A1 | 9/2019 | El Husseini et al. |
| 2019/0286973 | A1 | 9/2019 | Kovvuri et al. |
| 2019/0303198 | A1 | 10/2019 | Kim et al. |
| 2019/0311475 | A1 | 10/2019 | Hosoi |
| 2019/0355474 | A1 | 11/2019 | Mellem et al. |
| 2019/0370086 | A1 | 12/2019 | Heilper et al. |
| 2019/0370631 | A1 | 12/2019 | Fais et al. |
| 2019/0391811 | A1 | 12/2019 | Garegrat et al. |
| 2020/0034145 | A1 | 1/2020 | Bainville et al. |
| 2020/0117450 | A1 | 4/2020 | Mansell et al. |
| 2020/0117580 | A1 | 4/2020 | Lekivetz et al. |
| 2020/0202527 | A1* | 6/2020 | Choi .................. A61B 3/10 |
| 2020/0250545 | A1 | 8/2020 | Verrilli et al. |
| 2020/0380361 | A1 | 12/2020 | Tanach |
| 2021/0011846 | A1 | 1/2021 | Venkatesh et al. |
| 2021/0012178 | A1 | 1/2021 | Venkatesh et al. |
| 2021/0019591 | A1 | 1/2021 | Venkatesh et al. |
| 2021/0049231 | A1 | 2/2021 | Majnemer et al. |
| 2021/0150260 | A1 | 5/2021 | Wang et al. |
| 2021/0150317 | A1 | 5/2021 | Hou et al. |
| 2021/0192287 | A1* | 6/2021 | Dwivedi ............ G06F 9/3836 |
| 2021/0209451 | A1 | 7/2021 | Gu |
| 2021/0255860 | A1 | 8/2021 | Morrison et al. |
| 2021/0279629 | A1* | 9/2021 | Nelson ............... G06F 11/3428 |
| 2021/0319305 | A1 | 10/2021 | Kale et al. |
| 2021/0319821 | A1 | 10/2021 | Kale et al. |
| 2021/0319822 | A1 | 10/2021 | Kale et al. |
| 2021/0319823 | A1 | 10/2021 | Kale et al. |
| 2021/0320967 | A1 | 10/2021 | Kale et al. |
| 2021/0390076 | A1 | 12/2021 | Fang et al. |
| 2022/0044043 | A1 | 2/2022 | Zhu et al. |
| 2022/0044108 | A1 | 2/2022 | Kale |
| 2022/0067527 | A1 | 3/2022 | Xu et al. |
| 2022/0254400 | A1 | 8/2022 | Kale et al. |
| 2023/0004804 | A1 | 1/2023 | Kale et al. |
| 2023/0068106 | A1 | 3/2023 | Hu et al. |

OTHER PUBLICATIONS

Title: Deep Learning Accelerator and Random Access Memory with Separate Memory Access Connections, U.S. Appl. No. 16/844,993, filed Aug. 9, 2020 Inventors: Poorna Kale et al. Status: Docketed New Case—Ready for Examination Status Date: Aug. 20, 2021.

Title: Deep Learning Acelerator and Random Access Memory with a Camera Interface, U.S. Appl. No. 16/844,997, filed Apr. 9, 2020 Inventor: Poorna Kale et al. Status: Notice of Allowance Mailed—Application Recieved in Office of Publications Status Date: Feb. 2, 2022.

Title: Deep Learning Accelerator and Random Access Memory with a Camera Interface, U.S. Appl. No. 17/729,830, filed Apr. 26, 2022 Inventors: Poorna Kale et al. Status: Application Undergoing Preexam Processing Status Date: Apr. 26, 2022.

Title: System on a Chip with Deep Learning Accelerator and Random Access Memory, U.S. Appl. No. 16/845,002, filed Apr. 9, 2020 Inventors: Poorna Kale et al. Status: Docketed New Case—Ready for Examination Status Date: Aug. 20, 2021.

Title: Edge Server with Deep Learning Accelerator and Random Access Memory, U.S. Appl. No. 16/845,007, filed Apr. 9, 2020 Inventors: Poorna Kale et al. Status: Docketed New Case—Ready for Examination Status Date: May 1, 2020.

Title: Real Time Medical Image Processing Using Deep Learning Accelerator With Integrated Random Access Memory, U.S. Appl. No. 16/987,112, filed Aug. 6, 2020 Inventor: Poorna Kale Status: Docketed New Case—Ready for Examination Status Date: Sep. 24, 2020.

Chen, et al. "A Design of High-Speed Image Acquisition Card Based on PCI Express." International Conference on Computer Application and System Modeling, ICCASM, IEEE, 2010.

Marin, et al. "Image Processing System for PC Through the Enhanced Parallel Port." Proceedings of the IEEE International Symposium on Industrial Electronics, IEEE, 2010.

International Search Report and Written Opinion, PCT/US2021/044484, dated Nov. 16, 2021.

International Search Report and Written Opinion, PCT/US2021/025017, dated Jul. 13, 2021.

International Search Report and Written Opinion, PCT/US2021/025018, dated Jul. 13, 2021.

International Search Report and Written Opinion, PCT/US2021/026008, dated Jul. 22, 2021.

International Search Report and Written Opinion, PCT/US2021/026007, dated Jul. 22, 2021.

International Search Report and Written Opinion, PCT/US2021/026005, dated Jul. 23, 2021.

International Search Report and Written Opinion, PCT/US2021/026243, dated Jul. 27, 2021.

Title: Integrated Circuit Device with Deep Learning Accelerator and Random Access Memory, U.S. Appl. No. 16/844,988, filed Apr. 9, 2020 Intventors: Poorna Kale et al. Status: Application Dispatched from Preexam, Not Yet Docketed Status Date: Apr. 24, 2020.

Title: Deep Learning Accelerator and Random Access Memory with Separate Memory Access Connections, U.S. Appl. No. 16/844,993, filed Apr. 9, 2020 Inventors: Poorna Kale et al. Status: Application Dispatched from Preexam, Not Yet Docketed Status Date: Apr. 24, 2020.

Title: Deep Learning Accelerator and Random Access Memory with a Camera Interface, U.S. Appl. No. 16/844,997, filed Apr. 9, 2020 Inventors: Poorna Kale et al. Status: Application Dispatched from Preexam, Not Yet Docketed Status Date: Apr. 24, 2020.

Title: System on a Chip with Deep Learning Accelerator and Random Access Memory, U.S. Appl. No. 16/845,002, filed Apr. 9, 2020 Inventors: Poorna Kale et al. Status: Application Dispatched from Preexam, Not Yet Docketed Status Date: May 6, 2020.

Title: Real Time Medical Image Processing Using Deep Learning Accelerator With Integrated Random Access Memory, U.S. Appl. No. 16/987,112, filed Aug. 6, 2020 Inventor: Poorna Kale Status: Application Undergoing Preexam Processing Status Date: Aug. 6, 2020.

Title: Integrated Circuit Device with Deep Learning Accelerator and Random Access Memory, U.S. Appl. No. 16/844,988, filed Apr. 9,

(56) References Cited

OTHER PUBLICATIONS

2020 Status Date: Jan. 20, 2023 Inevntors: Poorna Kale, et al. Status: Non Final Action Mailed.
Title: Deep Learning Accelerator and Random Access Memroy with Separate Memory Access Connections, U.S. Appl. No. 16/844,993, filed Apr. 9, 2020 Status Date: Dec. 20, 2022 Inventors: Poorna Kale, et al. Status: Final Rejection Mailed.
Title: Deep Learning Accelerator and Random Access Memory with a Camera Interface, U.S. Appl. No. 16/844,997, filed Apr. 9, 2020 Status Date: May 18, 2022 Inventors: Poorna Kale, et al. Status: Patented Case.
Title: Deep Learning Accelerator and Random Access Memory with a Camera Interface, U.S. Appl. No. 17/729,830, filed Apr. 26, 2022 Status Date: Feb. 11, 2023 Inventors: Poorna Kale, et al. Status: Non Final Action Counted, Not Yet Mailed.
Title: System on a Chip with Deep Learning Accelerator and Random Access Memory, U.S. Appl. No. 16/845,002, filed Apr. 9, 2020 Status Date: Sep. 14, 2022 Inventors: Poorna Kale, et al. Status: Patented Case.
Title: System on a Chip with Deep Learning Accelerator and Random Access Memory, U.S. Appl. No. 17/940,343, filed Sep. 8, 2022 Status Date: Sep. 27, 2022 Inventors: Poorna Kale, et al. Status: Docketed New Case—Ready for Examination.
Title: Edge Server with Deep Learning Accelerator and Random Access Memory, U.S. Appl. No. 16/845,007, filed Apr. 9, 2020 Status Date: Dec. 22, 2022 Inventors: Poorna Kale, et al. Status: Docketed New Case—Ready for Examination.
Title: Real Time Medical Image Processing using Deep Learning Accelerator with Integrated Random Access Memory, U.S. Appl. No. 16/987,112, filed Aug. 6, 2020 Status Date: Sep. 24, 2020 Inventor: Poorna Kale Status: Docketed New Case—Ready for Examination.

* cited by examiner

PATIENT MONITORING USING EDGE SERVERS HAVING DEEP LEARNING ACCELERATOR AND RANDOM ACCESS MEMORY

FIELD OF THE TECHNOLOGY

At least some embodiments disclosed herein relate to patient monitoring in general and more particularly, but not limited to, monitoring using edge servers implemented using integrated circuit devices having accelerators for Artificial Neural Networks (ANNs), such as ANNs configured through machine learning and/or deep learning.

BACKGROUND

An Artificial Neural Network (ANN) uses a network of neurons to process inputs to the network and to generate outputs from the network.

For example, each neuron in the network receives a set of inputs. Some of the inputs to a neuron may be the outputs of certain neurons in the network; and some of the inputs to a neuron may be the inputs provided to the neural network. The input/output relations among the neurons in the network represent the neuron connectivity in the network.

For example, each neuron can have a bias, an activation function, and a set of synaptic weights for its inputs respectively. The activation function may be in the form of a step function, a linear function, a log-sigmoid function, etc. Different neurons in the network may have different activation functions.

For example, each neuron can generate a weighted sum of its inputs and its bias and then produce an output that is the function of the weighted sum, computed using the activation function of the neuron.

The relations between the input(s) and the output(s) of an ANN in general are defined by an ANN model that includes the data representing the connectivity of the neurons in the network, as well as the bias, activation function, and synaptic weights of each neuron. Based on a given ANN model, a computing device can be configured to compute the output(s) of the network from a given set of inputs to the network.

For example, the inputs to an ANN network may be generated based on camera inputs; and the outputs from the ANN network may be the identification of an item, such as an event or an object.

In general, an ANN may be trained using a supervised method where the parameters in the ANN are adjusted to minimize or reduce the error between known outputs associated with or resulted from respective inputs and computed outputs generated via applying the inputs to the ANN. Examples of supervised learning/training methods include reinforcement learning and learning with error correction.

Alternatively, or in combination, an ANN may be trained using an unsupervised method where the exact outputs resulted from a given set of inputs is not known before the completion of the training. The ANN can be trained to classify an item into a plurality of categories, or data points into clusters.

Multiple training algorithms can be employed for a sophisticated machine learning/training paradigm.

Deep learning uses multiple layers of machine learning to progressively extract features from input data. For example, lower layers can be configured to identify edges in an image; and higher layers can be configured to identify, based on the edges detected using the lower layers, items captured in the image, such as faces, objects, events, etc. Deep learning can be implemented via Artificial Neural Networks (ANNs), such as deep neural networks, deep belief networks, recurrent neural networks, and/or convolutional neural networks.

Deep learning has been applied to many application fields, such as computer vision, speech/audio recognition, natural language processing, machine translation, bioinformatics, drug design, medical image processing, games, etc.

BRIEF DESCRIPTION OF THE DRAWINGS

The embodiments are illustrated by way of example and not limitation in the figures of the accompanying drawings in which like references indicate similar elements.

DETAILED DESCRIPTION

Figure 1:
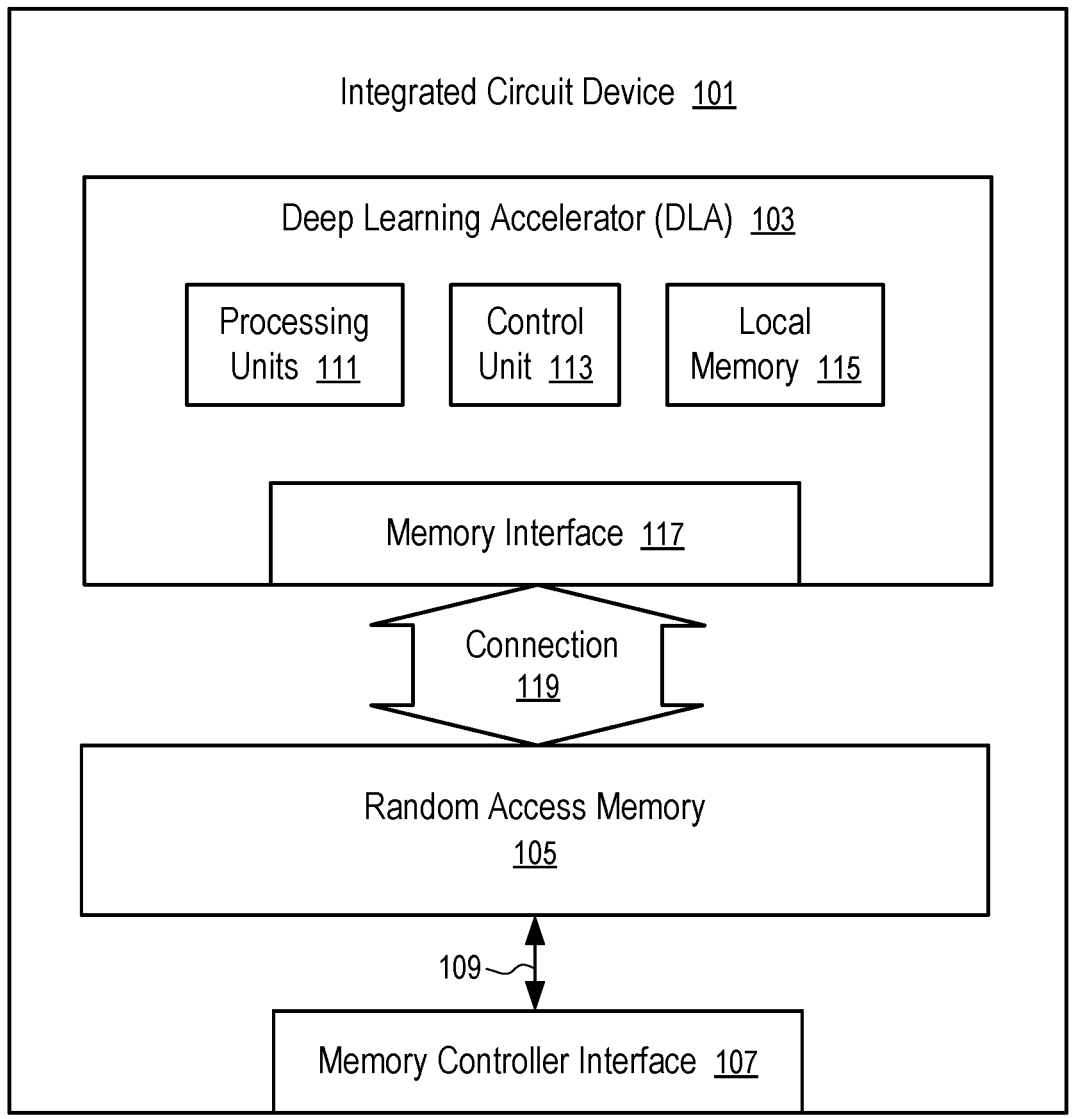
FIG. 1 shows an integrated circuit device having a Deep Learning Accelerator and random access memory configured according to one embodiment.

At least some embodiments disclosed herein provide a general-purpose integrated circuit device configured to perform computations of Artificial Neural Networks (ANNs) with reduced energy consumption and computation time. The integrated circuit device includes a Deep Learning Accelerator (DLA) and random access memory. The integrated circuit device can be configured with separate connections for concurrent access to the random access memory. The integrated circuit device can have a camera interface configured to receive image data directly from one or more cameras as input to an Artificial Neural Network (ANN) implemented in the integrated circuit device. Further, the integrated circuit device can include a Central Processing Unit (225) to form a system on a chip. Such integrated circuit devices can be used to implement edge servers to process data at a location close to the data source. For example, an edge server can be configured to process, using an Artificial Neural Network (ANN), real time data of a patient in assessing the current condition of the patient and in determining whether assistance and/or medical care is to be requested for the patient.

The Deep Learning Accelerator (DLA) includes a set of general-purpose, programmable hardware computing logic that is specialized and/or optimized to perform parallel vector and/or matrix calculations, including but not limited to multiplication and accumulation of vectors and/or matrices.

Further, the Deep Learning Accelerator (DLA) can include one or more Arithmetic-Logic Units (ALUs) to perform arithmetic and bitwise operations on integer binary numbers.

The Deep Learning Accelerator (DLA) is programmable via a set of instructions to perform the computations of an Artificial Neural Network (ANN).

The granularity of the Deep Learning Accelerator (DLA) operating on vectors and matrices corresponds to the largest unit of vectors/matrices that can be operated upon during the execution of one instruction by the Deep Learning Accelerator (DLA). During the execution of the instruction for a predefined operation on vector/matrix operands, elements of vector/matrix operands can be operated upon by the Deep Learning Accelerator (DLA) in parallel to reduce execution time and/or energy consumption associated with memory/data access. The operations on vector/matrix operands of the granularity of the Deep Learning Accelerator (DLA) can be used as building blocks to implement computations on vectors/matrices of larger sizes.

The implementation of a typical/practical Artificial Neural Network (ANN) involves vector/matrix operands having sizes that are larger than the operation granularity of the Deep Learning Accelerator (DLA). To implement such an Artificial Neural Network (ANN) using the Deep Learning Accelerator (DLA), computations involving the vector/matrix operands of large sizes can be broken down to the computations of vector/matrix operands of the granularity of the Deep Learning Accelerator (DLA). The Deep Learning Accelerator (DLA) can be programmed via instructions to carry out the computations involving large vector/matrix operands. For example, atomic computation capabilities of the Deep Learning Accelerator (DLA) in manipulating vectors and matrices of the granularity of the Deep Learning Accelerator (DLA) in response to instructions can be programmed to implement computations in an Artificial Neural Network (ANN).

In some implementations, the Deep Learning Accelerator (DLA) lacks some of the logic operation capabilities of a typical Central Processing Unit (CPU). However, the Deep Learning Accelerator (DLA) can be configured with sufficient logic units to process the input data provided to an Artificial Neural Network (ANN) and generate the output of the Artificial Neural Network (ANN) according to a set of instructions generated for the Deep Learning Accelerator (DLA). Thus, the Deep Learning Accelerator (DLA) can perform the computation of an Artificial Neural Network (ANN) with little or no help from a Central Processing Unit (CPU) or another processor. Optionally, a conventional general purpose processor can also be configured as part of the Deep Learning Accelerator (DLA) to perform operations that cannot be implemented efficiently using the vector/matrix processing units of the Deep Learning Accelerator (DLA), and/or that cannot be performed by the vector/matrix processing units of the Deep Learning Accelerator (DLA).

A typical Artificial Neural Network (ANN) can be described/specified in a standard format (e.g., Open Neural Network Exchange (ONNX)). A compiler can be used to convert the description of the Artificial Neural Network (ANN) into a set of instructions for the Deep Learning Accelerator (DLA) to perform calculations of the Artificial Neural Network (ANN). The compiler can optimize the set of instructions to improve the performance of the Deep Learning Accelerator (DLA) in implementing the Artificial Neural Network (ANN).

The Deep Learning Accelerator (DLA) can have local memory, such as registers, buffers and/or caches, configured to store vector/matrix operands and the results of vector/matrix operations. Intermediate results in the registers can be pipelined/shifted in the Deep Learning Accelerator (DLA) as operands for subsequent vector/matrix operations to reduce time and energy consumption in accessing memory/data and thus speed up typical patterns of vector/matrix operations in implementing a typical Artificial Neural Network (ANN). The capacity of registers, buffers and/or caches in the Deep Learning Accelerator (DLA) is typically insufficient to hold the entire data set for implementing the computation of a typical Artificial Neural Network (ANN). Thus, a random access memory coupled to the Deep Learning Accelerator (DLA) is configured to provide an improved data storage capability for implementing a typical Artificial Neural Network (ANN). For example, the Deep Learning Accelerator (DLA) loads data and instructions from the random access memory and stores results back into the random access memory.

The communication bandwidth between the Deep Learning Accelerator (DLA) and the random access memory is configured to optimize or maximize the utilization of the computation power of the Deep Learning Accelerator (DLA). For example, high communication bandwidth can be provided between the Deep Learning Accelerator (DLA) and the random access memory such that vector/matrix operands can be loaded from the random access memory into the Deep Learning Accelerator (DLA) and results stored back into the random access memory in a time period that is approximately equal to the time for the Deep Learning Accelerator (DLA) to perform the computations on the vector/matrix operands. The granularity of the Deep Learning Accelerator (DLA) can be configured to increase the ratio between the amount of computations performed by the Deep Learning Accelerator (DLA) and the size of the vector/matrix operands such that the data access traffic between the Deep Learning Accelerator (DLA) and the random access memory can be reduced, which can reduce the requirement on the communication bandwidth between the Deep Learning Accelerator (DLA) and the random access memory. Thus, the bottleneck in data/memory access can be reduced or eliminated.

In at least some embodiments, multiple connections are provided to allow different devices to access the random access memory in parallel for different purposes. For example, the random access memory can include a portion configured to store input to the Artificial Neural Network (ANN) and another portion configured to store output from the Artificial Neural Network (ANN). One connection to the random access memory can be used by the Central Processing Unit (CPU) or another processor to access the output from the Artificial Neural Network (ANN), while concurrently another connection to the random access memory can be used by a Direct Memory Access (DMA) controller to store into the random access memory input data for the Artificial Neural Network (ANN).

For example, the Central Processing Unit (CPU) can set up the Direct Memory Access (DMA) controller to write, into an input region of the random access memory, input data to be processed by the Artificial Neural Network (ANN). The completion of the Direct Memory Access (DMA) controller writing a set of input into the input region can trigger the Deep Learning Accelerator (DLA) to execute the instructions to implement Artificial Neural Network (ANN). The execution of the instructions results in the combination of the input with the matrices of the Artificial Neural Network (ANN) to generate output. The output is configured to be stored in another region of the random access memory for the Central Processing Unit (CPU).

Optionally, the model data of an Artificial Neural Network (ANN) can be stored in a further region of the random access memory. The model data can include the matrices identifying neural connectivity and synaptic weights of artificial neurons, states and/or properties of artificial neurons in the Artificial Neural Network (ANN). The model data can further include the instructions for the Deep Learning Accelerator (DLA) to implement the computation of the Artificial Neural Network (ANN). For example, a compiler can convert a description of the Artificial Neural Network (ANN) into the model data stored in the random access memory.

After the model data is stored in the random access memory and the Direct Memory Access (DMA) controller is configured to write input data into the random access memory, the Deep Learning Accelerator (DLA) and the Direct Memory Access (DMA) controller can process the input data using the Artificial Neural Network (ANN) without help from the Central Processing Unit (CPU). The output of the Artificial Neural Network (ANN) is automatically stored in the random access memory. The Central Processing Unit (CPU) can access the random access memory via a separate connection concurrently with the Direct Memory Access (DMA) controller providing input data to the Deep Learning Accelerator (DLA).

For example, a stream of input data to the Artificial Neural Network (ANN) can be configured in the form of a sequence of input data sets. Each input data set is for a set of input to the Artificial Neural Network (ANN) during a time slot. While the Deep Learning Accelerator (DLA) is computing the output from the current set of input, the Direct Memory Access (DMA) controller can store the next set of input into the random access memory; and the Central Processing Unit (CPU) can concurrently retrieve, from the random access memory, the output generated for the previous set of input.

Thus, the task of preparation and processing of input data to an Artificial Neural Network (ANN) can be offloaded from the Central Processing Unit (CPU). The combination of the Deep Learning Accelerator (DLA), random access memory and the Direct Memory Access (DMA) controller can function as an independent supplier of results from an Artificial Neural Network (ANN) to the Central Processing Unit (CPU). The Central Processing Unit (CPU) can retrieve a set of output at a time when the output is needed. The Central Processing Unit (CPU) can instruct the Direct Memory Access (DMA) controller to pause its operations in supplying input to the Artificial Neural Network (ANN) when output from the Artificial Neural Network (ANN) is not required. Subsequently, when output from the Artificial Neural Network (ANN) is needed, the Central Processing Unit (CPU) can instruct the Direct Memory Access (DMA) controller to resume its operations of loading input data into the random access memory.

Artificial Neural Networks (ANNs) can be used to process sensor data, such as images. For example, digital cameras can be used to generate images for computer vision and/or autonomous driving, flying, navigation, etc. For example, some sensor data can be converted into an image form for processing by an Artificial Neural Network (ANN). For example, radar, lidar, ultrasound scanner, medical imaging equipment, etc. can generate images for analysis by Artificial Neural Networks (ANNs) to recognize and/or classify features, objects, diseases, etc.

An integrated circuit device having a Deep Learning Accelerator and random access memory can be configured to include a camera interface to acquire image data as input to an Artificial Neural Network (ANN) implemented in the integrated circuit device.

For example, the camera interface can be implemented according to a Mobile Industry Processor Interface (MIPI) protocol to receive image data from an image sensor, a camera or another device that can generate images, such as radar, lidar, ultrasound scanner, medical imaging equipment. For example, the Mobile Industry Processor Interface (MIPI) protocol can include support of a camera command interface to control the operation of a camera, or an imaging device. The camera interface allows the integrated circuit device having a Deep Learning Accelerator and random access memory to control the receiving of image data as input for processing by an Artificial Neural Network (ANN). A camera or an image sensor/generator can stream its input data as images into the input region of the random access memory. The integrated circuit device automatically converts the input data according to an Artificial Neural Network (ANN) and stores the output from the Artificial Neural Network (ANN) in the random access memory. Since the integrated circuit device seamlessly acquires and converts the image data into Artificial Neural Network (ANN) outputs, data traffic to the Central Processing Unit (CPU) can be dramatically reduced.

The camera interface allows the integrated circuit device to be combined with an image generator as a smart sensor unit that automatically supplies the intelligent results from an Artificial Neural Network (ANN) in random access memory. Once the Central Processing Unit configures the integrated circuit device to operate, the computation tasks of acquiring input data and performing the computation involving the Artificial Neural Network (ANN) can be offloaded from the Central Processing Unit (CPU).

Optionally, the raw sensor/image data can be buffered in the random access memory for a period of time in a cyclic way such that if needed, the Central Processing Unit (CPU) can also access the raw sensor data within the period of time.

The logic circuit of a Central Processing Unit (CPU) can also be integrated into an integrated circuit device that has a Deep Learning Accelerator (DLP) and random access memory. The Central Processing Unit (CPU) and the Deep Learning Accelerator (DLP) can be configured to share the random access memory in the integrated circuit device. Since the integrated circuit device has a Central Processing Unit (CPU) and random access memory, the integrated circuit device can form a system on a chip and can be configured without an interface to an external memory bus.

For example, in such an integrated circuit device having a Central Processing Unit (CPU), applications can be programmed to run in the Central Processing Unit (CPU), where logical memory addresses used in a running instance of an application can be mapped via a memory controller of the Central Processing Unit to the physical memory address for accessing the random access memory. The Deep Learning Accelerator (DLP) can perform some or all of the computations involving an Artificial Neural Network (ANN) and can provide the output of the Artificial Neural Network (ANN) as input to the application(s) running in the Central Processing Unit (CPU). Thus, the integrated circuit device can be used to implement low cost, intelligent Internet of Things (IoTs), such as a surveillance camera.

For example, one or more sensors can be connected to an input/output interface of the integrated circuit device to provide sensor data as the input to an Artificial Neural Network (ANN) that has been trained to generate inference results. A description of the trained Artificial Neural Network (ANN) can be converted, using a compiler, into a set of instructions and matrix data. After storing the instructions and the matrix data in the random access memory, the Deep Learning Accelerator (DLP) can execute the instructions to combine the sensor data and the matrix data of the Artificial Neural Network (ANN) into high-level input for the Central Processing Unit. Optionally, the instructions executed by the Deep Learning Accelerator (DLP) can include calls to one or more routines executed in the Central Processing Unit. Signal lines can be implemented within the integrated circuit device to facilitate the calls. Thus, the Central Processing Unit in the integrated circuit device can optionally provide services to the Deep Learning Accelerator (DLP) in implementing the Artificial Neural Network (ANN).

The application to be executed by the Central Processing Unit can be programmed to read as input, from the random access memory, the inference results generated by the Artificial Neural Network (ANN). Therefore, the details of processing the sensor data using the Artificial Neural Network (ANN) can be shielded from the programming of the application.

An integrated circuit device having random access memory and a Deep Learning Accelerator (DLP), and optionally a Central Processing Unit, can be used to implement an edge server. The edge server can be used to process a stream of input data using an artificial neural network and generate inference results. The edge server can be configured to provide services in a computer network at a location close to the generator of the input data. For example, the inference result can be used by a user device and reduce the latency for the user device to obtain the inference result. For example, the inference result can be used by a server configured in a centralized location that is remote from the population of user devices and thus reduce the among of data traffic to remote, centralized server.

For example, such an integrated circuit device can be configured on a network communication device to implement an edge server. The network communication device can be a network interface card, a router, a network gateway, a hub of Internet of Things (IoTs), a wireless access point to a wired computer network or the Internet, a base station of a cellular communications network, etc. The edge server can be connected to a user device via a local area network, a wireless local area network (e.g., WiFi), a wireless personal area network (e.g., Bluetooth) such that input data traffic to the edge server is limited to a local area near the user device. The edge server can be further connected a remote, centralized server that services user devices. In general, some of the user devices may be optionally connected to the remote, centralized server directly without going through any edge server; and other user devices can be connected to the remote, centralized server via their edge servers. An edge server can provide at least some of the services of the remote, centralized server to one or more user devices in a local area, such as a user device connected to the edge server in a local area network, a wireless local area network (e.g., WiFi), or a wireless personal area network (e.g., Bluetooth). Thus, the deployment of the edge server can optimize latency for the user device(s) in obtaining services and/or data traffic in computer networks.

An edge server can be used to intelligently pre-processing data from user devices, recognize events and features from input data received from the user device(s), and generate intelligent, high level inputs for the remote, centralized server. The edge server can filter input data for the remote, centralized server, by converting the input data received from the user device(s) using an Artificial Neural Network (ANN). The Artificial Neural Network (ANN) can reduce a large amount of input data into recognized events and features that have a data size smaller than the input data. Input data of unrecognized events and features can be discarded at the edge server. Alternatively, input data of unrecognized events and features is transmitted to the remote, centralized server for further analysis. Based on the further analysis, the Artificial Neural Network (ANN) can be further trained to recognize events and features that are previously unrecognized. The Artificial Neural Network (ANN) implemented in the edge server can then be updated to improve its capability in recognizing events and features and thus reduce future data traffic to the remote, centralized server.

Further, the memory in the edge server can function as a data recorder to store input data associated with the recognized events and features within a period of time. Thus, within a period of time, when the input data of the recognized events and features are needed, the remote, centralized server can selective request the edge server to provide the input data.

The edge server can be configured to process the input data from medical devices and sensors that are connected to collect real-time information about a person, such as a patient in a hospital or a care center, or at home or another location. An Artificial Neural Network (ANN) implemented via the Deep Learning Accelerator (DLP) of the edge server can be trained via machine learning to combine the input data from the different medical devices and sensors to classify the status and condition of the patient. When a dangerous or unusual status is detected, the edge server can generate an alert for a caretaker, a nurse, and/or a medical doctor to intervene. Further, the Artificial Neural Network (ANN) can optionally generate a preliminary diagnosis of the condition of the patient for the caretaker, nurse, and/or medical doctor. The optional preliminary diagnosis and/or other inference results from the Artificial Neural Network (ANN) can speed up the preparation of the response to the dangerous or unusual situation. The intelligent inference made by the Artificial Neural Network (ANN) can reduce false alarms and/or improve accuracy in identifying situations that require the assistance from a caretaker, a nurse, and/or a medical doctor.

FIG. 1 shows an integrated circuit device (101) having a Deep Learning Accelerator (103) and random access memory (105) configured according to one embodiment.

The Deep Learning Accelerator (103) in FIG. 1 includes processing units (111), a control unit (113), and local memory (115). When vector and matrix operands are in the local memory (115), the controller unit (113) can use the processing units (111) to perform vector and matrix operations in accordance with instructions. Further, the controller unit (113) can load instructions and operands from the random access memory (105) through a memory interface (117) and a high speed/bandwidth connection (119).

The integrated circuit device (101) is configured to be enclosed within an integrated circuit package with pins or contacts for a memory controller interface (107).

The memory controller interface (107) is configured to support a standard memory access protocol such that the integrated circuit device (101) appears to a typical memory controller in a way same as a conventional random access memory device having no Deep Learning Accelerator (DLA) (103). For example, a memory controller external to the integrated circuit device (101) can access, using a standard memory access protocol through the memory controller interface (107), the random access memory (105) in the integrated circuit device (101).

The integrated circuit device (101) is configured with a high bandwidth connection (119) between the random access memory (105) and the Deep Learning Accelerator (DLA) (103) that are enclosed within the integrated circuit device (101). The bandwidth of the connection (119) is higher than the bandwidth of the connection (109) between the random access memory (105) and the memory controller interface (107).

In one embodiment, both the memory controller interface (107) and the memory interface (117) are configured to access the random access memory (105) via a same set of buses or wires. Thus, the bandwidth to access the random access memory (105) is shared between the memory interface (117) and the memory controller interface (107). Alternatively, the memory controller interface (107) and the memory interface (117) are configured to access the random access memory (105) via separate sets of buses or wires. Optionally, the random access memory (105) can include multiple sections that can be accessed concurrently via the connection (119). For example, when the memory interface (117) is accessing a section of the random access memory (105), the memory control interface (107) can concurrently access another section of the random access memory (105). For example, the different sections can be configured on different integrated circuit dies and/or different planes/banks of memory cells; and the different sections can be accessed in parallel to increase throughput in accessing the random access memory (105). For example, the memory controller interface (107) is configured to access one data unit of a predetermined size at a time; and the memory interface (117) is configured to access multiple data units, each of the same predetermined size, at a time.

In one embodiment, the random access memory (105) and the integrated circuit device (101) are configured on different integrated circuit dies configured within a same integrated circuit package. Further, the random access memory (105) can be configured on one or more integrated circuit dies that allows parallel access of multiple data elements concurrently.

In some implementations, the number of data elements of a vector or matrix that can be accessed in parallel over the connection (119) corresponds to the granularity of the Deep Learning Accelerator (DLA) operating on vectors or matrices. For example, when the processing units (111) can operated on a number of vector/matrix elements in parallel, the connection (119) is configured to load or store the same number, or multiples of the number, of elements via the connection (119) in parallel.

Optionally, the data access speed of the connection (119) can be configured based on the processing speed of the Deep Learning Accelerator (DLA) (103). For example, after an amount of data and instructions have been loaded into the local memory (115), the control unit (113) can execute an instruction to operate on the data using the processing units (111) to generate output. Within the time period of processing to generate the output, the access bandwidth of the connection (119) allows the same amount of data and instructions to be loaded into the local memory (115) for the next operation and the same amount of output to be stored back to the random access memory (105). For example, while the control unit (113) is using a portion of the local memory (115) to process data and generate output, the memory interface (117) can offload the output of a prior operation into the random access memory (105) from, and load operand data and instructions into, another portion of the local memory (115). Thus, the utilization and performance of the Deep Learning Accelerator (DLA) are not restricted or reduced by the bandwidth of the connection (119).

The random access memory (105) can be used to store the model data of an Artificial Neural Network (ANN) and to buffer input data for the Artificial Neural Network (ANN). The model data does not change frequently. The model data can include the output generated by a compiler for the Deep Learning Accelerator (DLA) to implement the Artificial Neural Network (ANN). The model data typically includes matrices used in the description of the Artificial Neural Network (ANN) and instructions generated for the Deep Learning Accelerator (DLA) (103) to perform vector/matrix operations of the Artificial Neural Network (ANN) based on vector/matrix operations of the granularity of the Deep Learning Accelerator (DLA) (103). The instructions operate not only on the vector/matrix operations of the Artificial Neural Network (ANN), but also on the input data for the Artificial Neural Network (ANN).

In one embodiment, when the input data is loaded or updated in the random access memory (105), the control unit (113) of the Deep Learning Accelerator (DLA) (103) can automatically execute the instructions for the Artificial Neural Network (ANN) to generate an output of the Artificial Neural Network (ANN). The output is stored into a predefined region in the random access memory (105). The Deep Learning Accelerator (DLA) (103) can executed the instructions without help from a Central Processing Unit (CPU). Thus, communications for the coordination between the Deep Learning Accelerator (DLA) (103) and a processor outside of the integrated circuit device (101) (e.g., a Central Processing Unit (CPU)) can be reduced or eliminated.

Optionally, the logic circuit of the Deep Learning Accelerator (DLA) (103) can be implemented via Complementary Metal Oxide Semiconductor (CMOS). For example, the technique of CMOS Under the Array (CUA) of memory cells of the random access memory (105) can be used to implement the logic circuit of the Deep Learning Accelerator (DLA) (103), including the processing units (111) and the control unit (113). Alternatively, the technique of CMOS in the Array of memory cells of the random access memory (105) can be used to implement the logic circuit of the Deep Learning Accelerator (DLA) (103).

In some implementations, the Deep Learning Accelerator (DLA) (103) and the random access memory (105) can be implemented on separate integrated circuit dies and connected using Through-Silicon Vias (TSV) for increased data bandwidth between the Deep Learning Accelerator (DLA) (103) and the random access memory (105). For example, the Deep Learning Accelerator (DLA) (103) can be formed on an integrated circuit die of a Field-Programmable Gate Array (FPGA) or Application Specific Integrated circuit (ASIC).

Alternatively, the Deep Learning Accelerator (DLA) (103) and the random access memory (105) can be configured in separate integrated circuit packages and connected via multiple point-to-point connections on a printed circuit board (PCB) for parallel communications and thus increased data transfer bandwidth.

The random access memory (105) can be volatile memory or non-volatile memory, or a combination of volatile memory and non-volatile memory. Examples of non-volatile memory include flash memory, memory cells formed based on negative-and (NAND) logic gates, negative-or (NOR) logic gates, Phase-Change Memory (PCM), magnetic memory (MRAM), resistive random-access memory, cross point storage and memory devices. A cross point memory device can use transistor-less memory elements, each of which has a memory cell and a selector that are stacked together as a column. Memory element columns are connected via two lays of wires running in perpendicular directions, where wires of one lay run in one direction in the layer that is located above the memory element columns, and wires of the other lay run in another direction and are located below the memory element columns. Each memory element can be individually selected at a cross point of one wire on each of the two layers. Cross point memory devices are fast and non-volatile and can be used as a unified memory pool for processing and storage. Further examples of non-volatile memory include Read-Only Memory (ROM), Programmable Read-Only Memory (PROM), Erasable Programmable Read-Only Memory (EPROM) and Electronically Erasable Programmable Read-Only Memory (EEPROM) memory, etc. Examples of volatile memory include Dynamic Random-Access Memory (DRAM) and Static Random-Access Memory (SRAM).

For example, non-volatile memory can be configured to implement at least a portion of the random access memory (105). The non-volatile memory in the random access memory (105) can be used to store the model data of an Artificial Neural Network (ANN). Thus, after the integrated circuit device (101) is powered off and restarts, it is not necessary to reload the model data of the Artificial Neural Network (ANN) into the integrated circuit device (101). Further, the non-volatile memory can be programmable/rewritable. Thus, the model data of the Artificial Neural Network (ANN) in the integrated circuit device (101) can be updated or replaced to implement an update Artificial Neural Network (ANN), or another Artificial Neural Network (ANN).

The processing units (111) of the Deep Learning Accelerator (DLA) (103) can include vector-vector units, matrix-vector units, and/or matrix-matrix units. Examples of units configured to perform for vector-vector operations, matrix-vector operations, and matrix-matrix operations are discussed below in connection with FIGS. 2-4.

Figure 2:
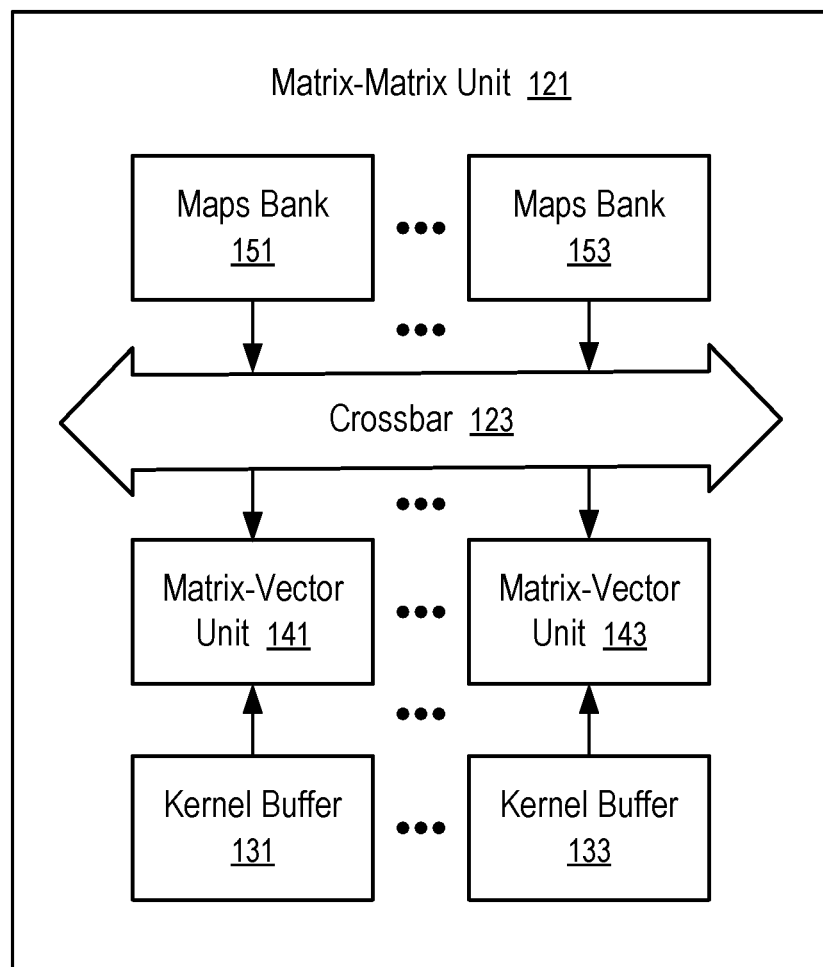
FIG. 2 shows a processing unit configured to perform matrix-matrix operations according to one embodiment.

FIG. 2 shows a processing unit (121) configured to perform matrix-matrix operations according to one embodiment. For example, the matrix-matrix unit (121) of FIG. 2 can be used as one of the processing units (111) of the Deep Learning Accelerator (DLA) (103) of FIG. 1.

In FIG. 2, the matrix-matrix unit (121) includes multiple kernel buffers (131 to 133) and multiple the maps banks (151 to 153). Each of the maps banks (151 to 153) stores one vector of a matrix operand that has multiple vectors stored in the maps banks (151 to 153) respectively; and each of the kernel buffers (131 to 133) stores one vector of another matrix operand that has multiple vectors stored in the kernel buffers (131 to 133) respectively. The matrix-matrix unit (121) is configured to perform multiplication and accumulation operations on the elements of the two matrix operands, using multiple matrix-vector units (141 to 143) that operate in parallel.

A cross bar (123) connects the maps banks (151 to 153) to the matrix-vector units (141 to 143). The same matrix operand stored in the maps bank (151 to 153) is provided via the crossbar (123) to each of the matrix-vector units (141 to 143); and the matrix-vector units (141 to 143) receives data elements from the maps banks (151 to 153) in parallel. Each of the kernel buffers (131 to 133) is connected to a respective one in the matrix-vector units (141 to 143) and provides a vector operand to the respective matrix-vector unit. The matrix-vector units (141 to 143) operate concurrently to compute the operation of the same matrix operand, stored in the maps banks (151 to 153) multiplied by the corresponding vectors stored in the kernel buffers (131 to 133). For example, the matrix-vector unit (141) performs the multiplication operation on the matrix operand stored in the maps banks (151 to 153) and the vector operand stored in the kernel buffer (131), while the matrix-vector unit (143) is concurrently performing the multiplication operation on the matrix operand stored in the maps banks (151 to 153) and the vector operand stored in the kernel buffer (133).

Figure 3:
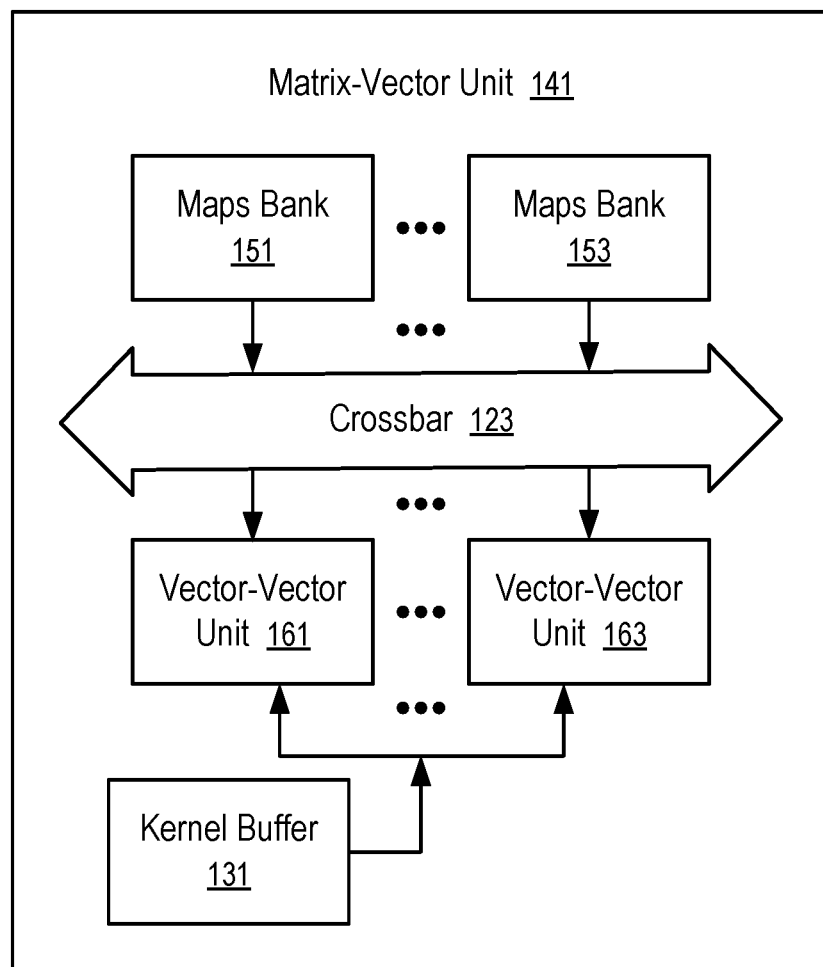
FIG. 3 shows a processing unit configured to perform matrix-vector operations according to one embodiment.

Each of the matrix-vector units (141 to 143) in FIG. 2 can be implemented in a way as illustrated in FIG. 3.

FIG. 3 shows a processing unit (141) configured to perform matrix-vector operations according to one embodiment. For example, the matrix-vector unit (141) of FIG. 3 can be used as any of the matrix-vector units in the matrix-matrix unit (121) of FIG. 2.

In FIG. 3, each of the maps banks (151 to 153) stores one vector of a matrix operand that has multiple vectors stored in the maps banks (151 to 153) respectively, in a way similar to the maps banks (151 to 153) of FIG. 2. The crossbar (123) in FIG. 3 provides the vectors from the maps banks (151) to the vector-vector units (161 to 163) respectively. A same vector stored in the kernel buffer (131) is provided to the vector-vector units (161 to 163).

The vector-vector units (161 to 163) operate concurrently to compute the operation of the corresponding vector operands, stored in the maps banks (151 to 153) respectively, multiplied by the same vector operand that is stored in the kernel buffer (131). For example, the vector-vector unit (161) performs the multiplication operation on the vector operand stored in the maps bank (151) and the vector operand stored in the kernel buffer (131), while the vector-vector unit (163) is concurrently performing the multiplication operation on the vector operand stored in the maps bank (153) and the vector operand stored in the kernel buffer (131).

When the matrix-vector unit (141) of FIG. 3 is implemented in a matrix-matrix unit (121) of FIG. 2, the matrix-vector unit (141) can use the maps banks (151 to 153), the crossbar (123) and the kernel buffer (131) of the matrix-matrix unit (121).

Figure 4:
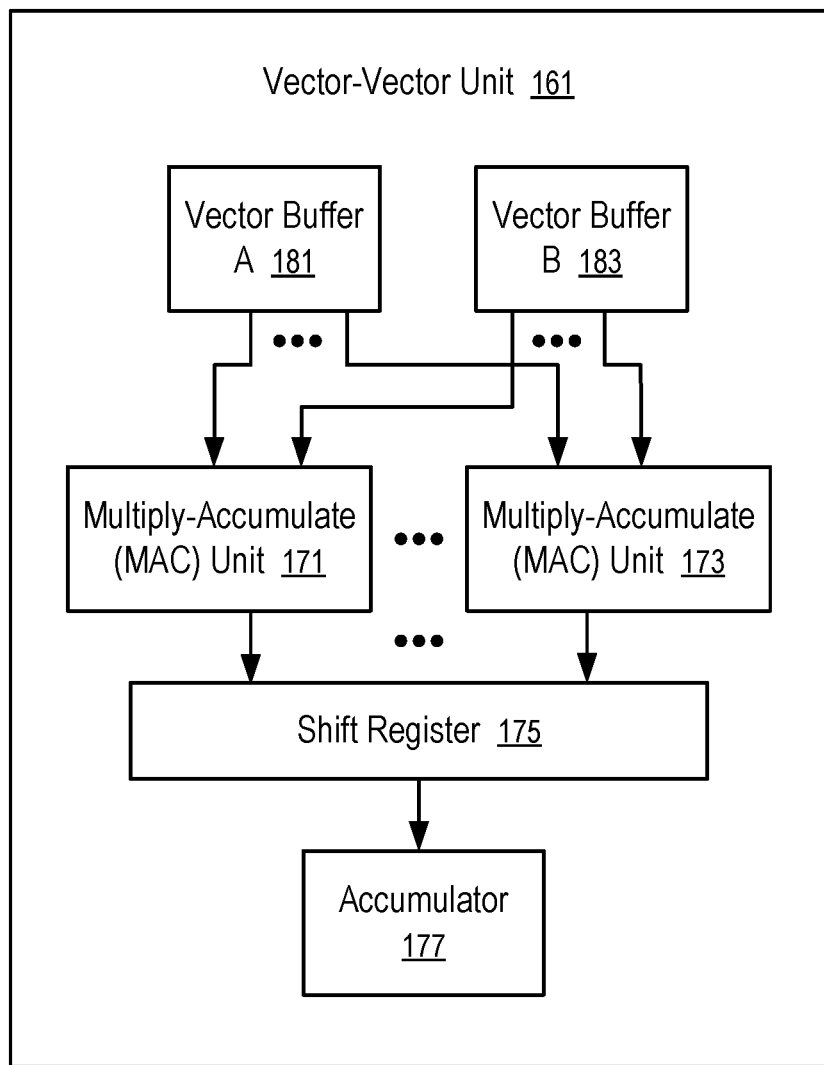
FIG. 4 shows a processing unit configured to perform vector-vector operations according to one embodiment.

Each of the vector-vector units (161 to 163) in FIG. 3 can be implemented in a way as illustrated in FIG. 4.

FIG. 4 shows a processing unit (161) configured to perform vector-vector operations according to one embodiment. For example, the vector-vector unit (161) of FIG. 4 can be used as any of the vector-vector units in the matrix-vector unit (141) of FIG. 3.

In FIG. 4, the vector-vector unit (161) has multiple multiply-accumulate (MAC) units (171 to 173). Each of the multiply-accumulate (MAC) units (171 to 173) can receive two numbers as operands, perform multiplication of the two numbers, and add the result of the multiplication to a sum maintained in the multiply-accumulate (MAC) unit.

Each of the vector buffers (181 and 183) stores a list of numbers. A pair of numbers, each from one of the vector buffers (181 and 183), can be provided to each of the multiply-accumulate (MAC) units (171 to 173) as input. The multiply-accumulate (MAC) units (171 to 173) can receive multiple pairs of numbers from the vector buffers (181 and 183) in parallel and perform the multiply-accumulate (MAC) operations in parallel. The outputs from the multiply-accumulate (MAC) units (171 to 173) are stored into the shift register (175); and an accumulator (177) computes the sum of the results in the shift register (175).

When the vector-vector unit (161) of FIG. 4 is implemented in a matrix-vector unit (141) of FIG. 3, the vector-vector unit (161) can use a maps bank (e.g., 151 or 153) as one vector buffer (181), and the kernel buffer (131) of the matrix-vector unit (141) as another vector buffer (183).

The vector buffers (181 and 183) can have a same length to store the same number/count of data elements. The length can be equal to, or the multiple of, the count of multiply-accumulate (MAC) units (171 to 173) in the vector-vector unit (161). When the length of the vector buffers (181 and 183) is the multiple of the count of multiply-accumulate (MAC) units (171 to 173), a number of pairs of inputs, equal to the count of the multiply-accumulate (MAC) units (171 to 173), can be provided from the vector buffers (181 and 183) as inputs to the multiply-accumulate (MAC) units (171 to 173) in each iteration; and the vector buffers (181 and 183) feed their elements into the multiply-accumulate (MAC) units (171 to 173) through multiple iterations.

In one embodiment, the communication bandwidth of the connection (119) between the Deep Learning Accelerator (DLA) (103) and the random access memory (105) is sufficient for the matrix-matrix unit (121) to use portions of the random access memory (105) as the maps banks (151 to 153) and the kernel buffers (131 to 133).

In another embodiment, the maps banks (151 to 153) and the kernel buffers (131 to 133) are implemented in a portion of the local memory (115) of the Deep Learning Accelerator (DLA) (103). The communication bandwidth of the connection (119) between the Deep Learning Accelerator (DLA) (103) and the random access memory (105) is sufficient to load, into another portion of the local memory (115), matrix operands of the next operation cycle of the matrix-matrix unit (121), while the matrix-matrix unit (121) is performing the computation in the current operation cycle using the maps banks (151 to 153) and the kernel buffers (131 to 133) implemented in a different portion of the local memory (115) of the Deep Learning Accelerator (DLA) (103).

Figure 5:
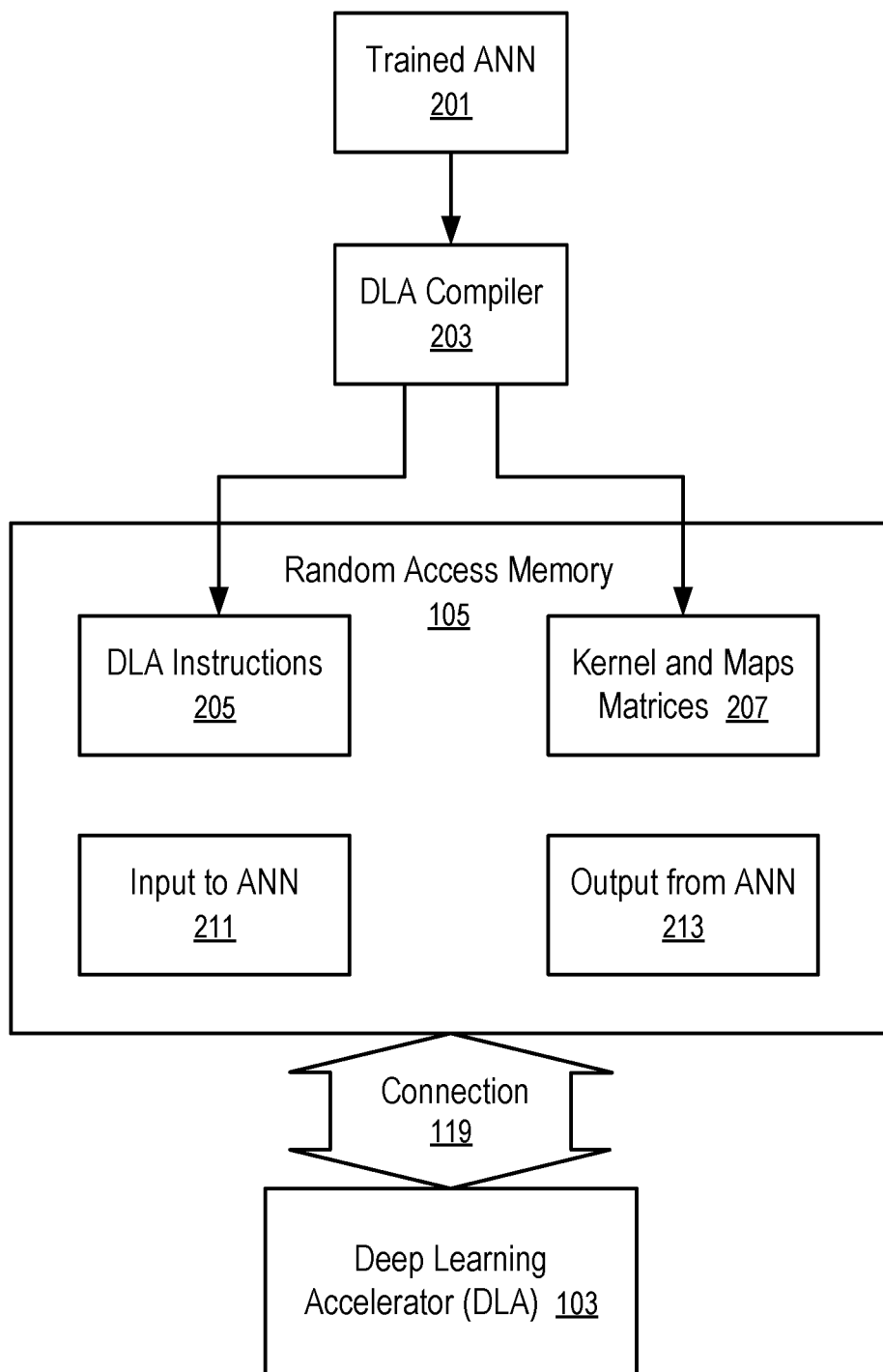
FIG. 5 shows a Deep Learning Accelerator and random access memory configured to autonomously apply inputs to a trained Artificial Neural Network according to one embodiment.

FIG. 5 shows a Deep Learning Accelerator and random access memory configured to autonomously apply inputs to a trained Artificial Neural Network according to one embodiment.

An Artificial Neural Network (ANN) (201) that has been trained through machine learning (e.g., deep learning) can be described in a standard format (e.g., Open Neural Network Exchange (ONNX)). The description of the trained ANN (201) in the standard format identifies the properties of the artificial neurons and their connectivity.

In FIG. 5, a Deep Learning Accelerator (DLA) compiler (203) converts trained ANN (201) by generating instructions (205) for a Deep Learning Accelerator (DLA) (103) and matrices (207) corresponding to the properties of the artificial neurons and their connectivity. The instructions (205) and the matrices (207) generated by the DLA compiler (203) from the trained ANN (201) can be stored in random access memory (105) for the Deep Learning Accelerator (DLA) (103).

For example, the random access memory (105) and the Deep Learning Accelerator (DLA) (103) can be connected via a high bandwidth connection (119) in a way as in the integrated circuit device (101) of FIG. 1. The autonomous computation of FIG. 5 based on the instructions (205) and the matrices (207) can be implemented in the integrated circuit device (101) of FIG. 1. Alternatively, the random access memory (105) and the Deep Learning Accelerator (DLA) (103) can be configured on a printed circuit board with multiple point to point serial buses running in parallel to implement the connection (119).

In FIG. 5, after the results of the DLA compiler (203) are stored in the random access memory (105), the application of the trained ANN (201) to process an input (211) to the trained ANN (201) to generate the corresponding output (213) of the trained ANN (213) can be triggered by the presence of the input (211) in the random access memory (105), or another indication provided in the random access memory (105).

In response, the Deep Learning Accelerator (DLA) (103) executes the instructions (205) to combine the input (211) and the matrices (207). The execution of the instructions (205) can include the generation of maps matrices for the maps banks (151 to 153) of one or more matrix-matrix units (e.g., 121) of the Deep Learning Accelerator (DLA) (103).

In some embodiments, the inputs to ANN (211) is in the form of an initial maps matrix. Portions of the initial maps matrix can be retrieved from the random access memory (105) as the matrix operand stored in the maps banks (151 to 153) of a matrix-matrix unit (121). Alternatively, the DLA instructions (205) also include instructions for the Deep Learning Accelerator (DLA) (103) to generate the initial maps matrix from the input (211).

According to the DLA instructions (205), the Deep Learning Accelerator (DLA) (103) loads matrix operands into the kernel buffers (131 to 133) and maps banks (151 to 153) of its matrix-matrix unit (121). The matrix-matrix unit (121) performs the matrix computation on the matrix operands. For example, the DLA instructions (205) break down matrix computations of the trained ANN (201) according to the computation granularity of the Deep Learning Accelerator (DLA) (103) (e.g., the sizes/dimensions of matrices that loaded as matrix operands in the matrix-matrix unit (121)) and applies the input feature maps to the kernel of a layer of artificial neurons to generate output as the input for the next layer of artificial neurons.

Upon completion of the computation of the trained ANN (201) performed according to the instructions (205), the Deep Learning Accelerator (DLA) (103) stores the output (213) of the ANN (201) at a pre-defined location in the random access memory (105), or at a location specified in an indication provided in the random access memory (105) to trigger the computation.

When the technique of FIG. 5 is implemented in the integrated circuit device (101) of FIG. 1, an external device connected to the memory controller interface (107) can write the input (211) into the random access memory (105) and trigger the autonomous computation of applying the input (211) to the trained ANN (201) by the Deep Learning Accelerator (DLA) (103). After a period of time, the output (213) is available in the random access memory (105); and the external device can read the output (213) via the memory controller interface (107) of the integrated circuit device (101).

For example, a predefined location in the random access memory (105) can be configured to store an indication to trigger the autonomous execution of the instructions (205) by the Deep Learning Accelerator (DLA) (103). The indication can optionally include a location of the input (211) within the random access memory (105). Thus, during the autonomous execution of the instructions (205) to process the input (211), the external device can retrieve the output generated during a previous run of the instructions (205), and/or store another set of input for the next run of the instructions (205).

Optionally, a further predefined location in the random access memory (105) can be configured to store an indication of the progress status of the current run of the instructions (205). Further, the indication can include a prediction of the completion time of the current run of the instructions (205) (e.g., estimated based on a prior run of the instructions (205)). Thus, the external device can check the completion status at a suitable time window to retrieve the output (213).

In some embodiments, the random access memory (105) is configured with sufficient capacity to store multiple sets of inputs (e.g., 211) and outputs (e.g., 213). Each set can be configured in a predetermined slot/area in the random access memory (105).

The Deep Learning Accelerator (DLA) (103) can execute the instructions (205) autonomously to generate the output (213) from the input (211) according to matrices (207) stored in the random access memory (105) without helps from a processor or device that is located outside of the integrated circuit device (101).

In a method according to one embodiment, random access memory (103) of a computing device (e.g., 101) can be accessed using an interface (107) of the computing device (e.g., 101) to a memory controller. The computing device (e.g., 101) can have processing units (e.g., 111) configured to perform at least computations on matrix operands, such as a matrix operand stored in maps banks (151 to 153) and a matrix operand stored in kernel buffers (131 to 133).

For example, the computing device (e.g., 101) can be enclosed within an integrated circuit package; and a set of connections can connect the interface (107) to the memory controller that is located outside of the integrated circuit package.

Instructions (205) executable by the processing units (e.g., 111) can be written into the random access memory (105) through the interface (107).

Matrices (207) of an Artificial Neural Network (201) can be written into the random access memory (105) through the interface (107). The matrices (207) identify the property and/or state of the Artificial Neural Network (201).

Optionally, at least a portion of the random access memory (105) is non-volatile and configured to store the instructions (205) and the matrices (207) of the Artificial Neural Network (201).

First input (211) to the Artificial Neural Network can be written into the random access memory (105) through the interface (107).

An indication is provided in the random access memory (105) to cause the processing units (111) to start execution of the instructions (205). In response to the indication, the processing units (111) execute the instructions to combine the first input (211) with the matrices (207) of the Artificial Neural Network (201) to generate first output (213) from the Artificial Neural Network (201) and store the first output (213) in the random access memory (105).

For example, the indication can be an address of the first input (211) in the random access memory (105); and the indication can be stored a predetermined location in the random access memory (105) to cause the initiation of the execution of the instructions (205) for the input (211) identified by the address. Optionally, the indication can also include an address for storing the output (213).

The first output (213) can be read, through the interface (107), from the random access memory (105).

For example, the computing device (e.g., 101) can have a Deep Learning Accelerator (103) formed on a first integrated circuit die and the random access memory (105) formed on one or more second integrated circuit dies. The connection (119) between the first integrated circuit die and the one or more second integrated circuit dies can include Through-Silicon Vias (TSVs) to provide high bandwidth for memory access.

For example, a description of the Artificial Neural Network (201) can be converted using a compiler (203) into the instructions (205) and the matrices (207). The combination of the instructions (205) and the matrices (207) stored in the random access memory (105) and the Deep Learning Accelerator (103) provides an autonomous implementation of the Artificial Neural Network (201) that can automatically convert input (211) to the Artificial Neural Network (201) to its output (213).

For example, during a time period in which the Deep Learning Accelerator (103) executes the instructions (205) to generate the first output (213) from the first input (211) according to the matrices (207) of the Artificial Neural Network (201), the second input to Artificial Neural Network (201) can be written into the random access memory (105) through the interface (107) at an alternative location. After the first output (213) is stored in the random access memory (105), an indication can be provided in the random access memory to cause the Deep Learning Accelerator (103) to again start the execution of the instructions and generate second output from the second input.

During the time period in which the Deep Learning Accelerator (103) executes the instructions (205) to generate the second output from the second input according to the matrices (207) of the Artificial Neural Network (201), the first output (213) can be read from the random access memory (105) through the interface (107); and a further input can be written into the random access memory to replace the first input (211), or written at a different location. The process can be repeated for a sequence of inputs.

The Deep Learning Accelerator (103) can include at least one matrix-matrix unit (121) that can execute an instruction on two matrix operands. The two matrix operands can be a first matrix and a second matrix. Each of two matrices has a plurality of vectors. The matrix-matrix unit (121) can include a plurality of matrix-vector units (141 to 143) configured to operate in parallel. Each of the matrix-vector units (141 to 143) are configured to operate, in parallel with other matrix-vector units, on the first matrix and one vector from second matrix. Further, each of the matrix-vector units (141 to 143) can have a plurality of vector-vector units (161 to 163) configured to operate in parallel. Each of the vector-vector units (161 to 163) is configured to operate, in parallel with other vector-vector units, on a vector from the first matrix and a common vector operand of the corresponding matrix-vector unit. Further, each of the vector-vector units (161 to 163) can have a plurality of multiply-accumulate units (171 to 173) configured to operate in parallel.

The Deep Learning Accelerator (103) can have local memory (115) and a control unit (113) in addition to the processing units (111). The control unit (113) can load instructions (205) and matrix operands (e.g., 207) from the random access memory (105) for execution by the processing units (111). The local memory can cache matrix operands used by the matrix-matrix unit. The connection (119) can be configured with a bandwidth sufficient to load a set of matrix operands from the random access memory (105) to the local memory (115) during a time period in which the matrix-matrix unit performs operations on two other matrix operands. Further, during the time period, the bandwidth is sufficient to store a result, generated by the matrix-matrix unit (121) in a prior instruction execution, from the local memory (115) to the random access memory (105).

Figure 6:
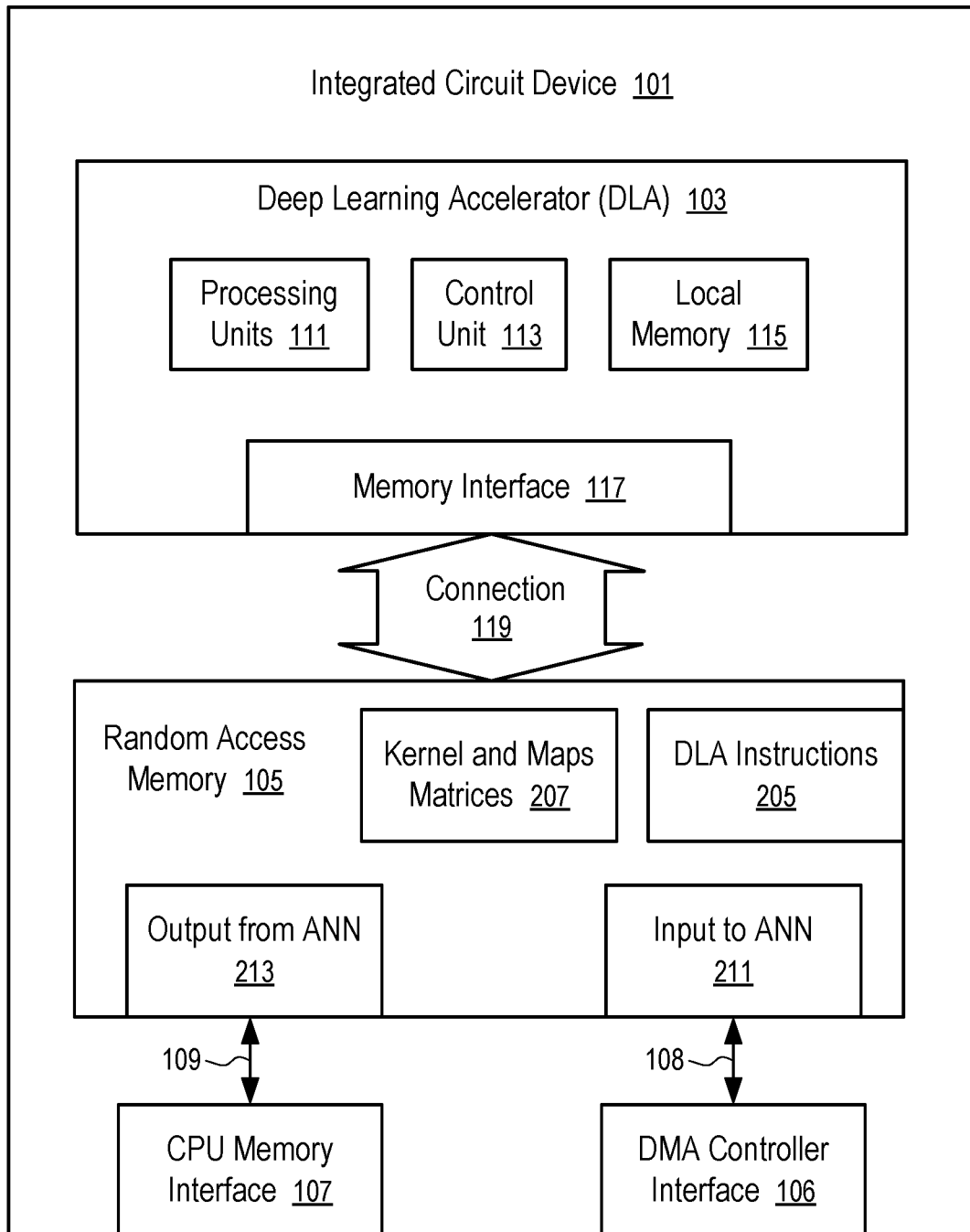
FIG. 6 shows an integrated circuit device having a Deep Learning Accelerator and random access memory configured with separate memory access connections according to one embodiment.

FIG. 6 shows an integrated circuit device (101) having a Deep Learning Accelerator (103) and random access memory (105) configured with separate memory access connections according to one embodiment.

For example, the Deep Learning Accelerator (103), the random access memory (105), and the connection (119) of the integrated circuit device (101) of FIG. 6 can be configured in a way similar to those illustrated in FIG. 1 and/or FIG. 5.

The integrated circuit device (101) of FIG. 6 has two external interfaces (106 and 107) that can be used to access the random access memory (105) concurrently.

For example, the random access memory (105) can have at least two portions that can be accessed concurrently and independently from reach other. Such portions can be configured on separate integrated circuit dies, or in separate planes or blocks of memory cells form on a same integrated circuit die. One portion is configured to store input (211) to the Artificial Neural Network (ANN) (201); and another portion is configured to store output (213) from the Artificial Neural Network (ANN) (201). The two external interfaces (106 and 107) configured with separate connections (108 and 109) to the portions for the input (211) and output (213) respectively. Thus, different devices external to the integrated circuit (101) can use the separate external interfaces (106 and 107) of the integrated circuit device (101) to access its random access memory (105) concurrently.

For example, a memory controller of a Central Processing Unit (CPU) can be connected to the CPU memory interface (107) to read prior output from the Artificial Neural Network (ANN) (201), while a Direct Memory Access (DMA) controller can be connected to the DMA controller interface (106) to write next input to the Artificial Neural Network (ANN) (201) concurrently.

In one embodiment, the connections (108 and 109) have separate sets of buses or wires. Thus, the external interfaces (106 and 107) do not share buses or wires in accessing the different portions of the random access memory (105) for the input (211) and the output (213). Alternatively, an access controller is configured to use separate buffers for the interfaces (106 and 107) and use the high bandwidth connection (119) to transfer data between the random access memory (105) and the buffers for the interfaces (106 and 107) such that the interfaces (106 and 107) can service write and read requests concurrently. Since the bandwidth of the connection (119) is substantially higher than the bandwidth used by the connections (108 and 109) to the external interfaces (106 and 107) of the integrated circuit device (101), a small portion of the bandwidth can be allocated to the connections (108 and 109). For example, the interfaces (106 and 107) can be connected to the memory interface (117) of the Deep Learning Accelerator (DLA) (103) to access the random access memory (105) via the connection (119).

Optionally, the memory interface (117) of the Deep Learning Accelerator (DLA) (103), the interface (107) to the memory controller of the Central Processing Unit (CPU), and the interface (106) can be configured to access the random access memory (105) concurrently.

For example, the random access memory (105) can be configured with at multiple sets of input/output memory. Each set can be selectively configured to service the memory interface (117) or service the external interfaces (106 and 107). When a set of input/output memory is selected to service the memory interface (117), the connection (119) allows the Deep Learning Accelerator (DLA) (103) to access input (e.g., 211) stored in the set and to store output (e.g., 213) from the Artificial Neural Network (ANN) (201) to the set. When a set of input/output memory is selected to service the external interfaces (106 and 107), the input (e.g., 211) and the output (e.g., 213) in different memory regions can be accessed concurrently by the separate external interfaces (106 and 107). While one set of input/output memory is allocated for the Deep Learning Accelerator (DLA) (103) to process a set of input (e.g., 211) and generate a corresponding set of output (e.g., 213), one or more sets of input/output memory can be concurrently made accessible to the external interfaces (106 and 107).

In a method according to one embodiment, an integrated circuit device (101) stores matrices (207) of an Artificial Neural Network (201) and instructions (205). The instructions (205) are executable by at least one processing unit (111) enclosed within the integrated circuit device (101) to implement the Artificial Neural Network (201) using the matrices (207). The integrated circuit device (101), or the alternatively packaged computing device on a printed circuit board, has random access memory.

The random access memory (105) enclosed within the integrated circuit device (101) stores first input to the Artificial Neural Network (201); and the at least one processing unit (111) is caused or used to execute the instructions (205) in generating first output from the first input stored in the random access memory (105). The first output is stored in the random access memory (105).

Subsequently, the random access memory (105) enclosed within the integrated circuit device (101) further stores second input to the Artificial Neural Network (201); and the at least one processing unit (111) is caused or used to execute the instructions (205) in generating second output from the second input stored in the random access memory (105).

While the at least one processing unit (111) is executing the instructions (205) to generate the second output from the second input, an external device (e.g., a direct memory access controller) writes, through a first interface (106) of the integrated circuit device (101), third input to the Artificial Neural Network (201) into the random access memory (105) in the integrated circuit device (101). At the same time, another external device (e.g., a Central Processing Unit) reads the first output from the random access memory (105), through a second interface (107) of the integrated circuit device (101) and concurrently with the writing of the third input.

For example, the writing of the third input can be performed through the first interface (106) connected to a direct memory access controller; and the reading of the first output can be performed through the second interface (107) connected to a Central Processing Unit.

For example, the integrated circuit device (101) can be enclosed within an integrated circuit package and has a Deep Learning Accelerator (103) with processing units (111), a control unit (113) and local memory (115). The processing units (111) include at least a matrix-matrix unit (121) configured to execute an instruction having two matrix operands. The matrix-matrix unit (121) includes a plurality of matrix-vector units (141 to 143) configured to operate in parallel. Each of the matrix-vector units (141 to 143) includes a plurality of vector-vector units (161 to 163) configured to operate in parallel. Each of the vector-vector units (161 to 163) includes a plurality of multiply-accumulate units (171 to 173) configured to operate in parallel.

For example, a compiler (203) can be used to convert a description of the Artificial Neural Network (201) into the instructions (205) and the matrices (207) to implement the Artificial Neural Network (101) using the Deep Learning Accelerator (103).

In one implementation, the reading of the first output through the second interface (107), the writing of the third input through the first interface (106), the Deep Learning Accelerator (103) reading a portion of the second input, and the Deep Learning Accelerator (103) writing a portion of the second output into the random access memory can be performed in parallel and concurrently.

For example, the random access memory (105) can have multiple portions that are capable of being used concurrently and independent from each other. A first portion is configured to store the first output from the Artificial Neural Network (201); a second portion configured to store third input to the Artificial Neural Network (201); a third portion configured to store the second output from the Artificial Neural Network (201); and a fourth portion configured to store the second input to the Artificial Neural Network (201). When the third and fourth portions are being used by the Deep Learning Accelerator 103) in execution of the instructions (205), the first interface and the second interface can be connected concurrently to the first portion and second portion respectively.

For example, the different portions can be configured on separate integrated circuit dies (or planes or blocks) that can operate independent from each other in parallel. The first interface and the second interface can share no connections to the first portion and the second portion.

The integrated circuit device (101) can be enclosed within a single integrated circuit package, with a first set of connectors configured to couple the first interface (106) to the direct memory access controller and a second set of connectors configured to couple the second interface (107) to the Central Processing Unit.

In some implementations, the Deep Learning Accelerator (103) has a memory interface (117) with a high bandwidth connection (119) to the random access memory (105); and the first interface (106) and the second interface (107) are connected to the random access memory (105) via the memory interface (117) of the Deep Learning Accelerator (117).

Figure 7:
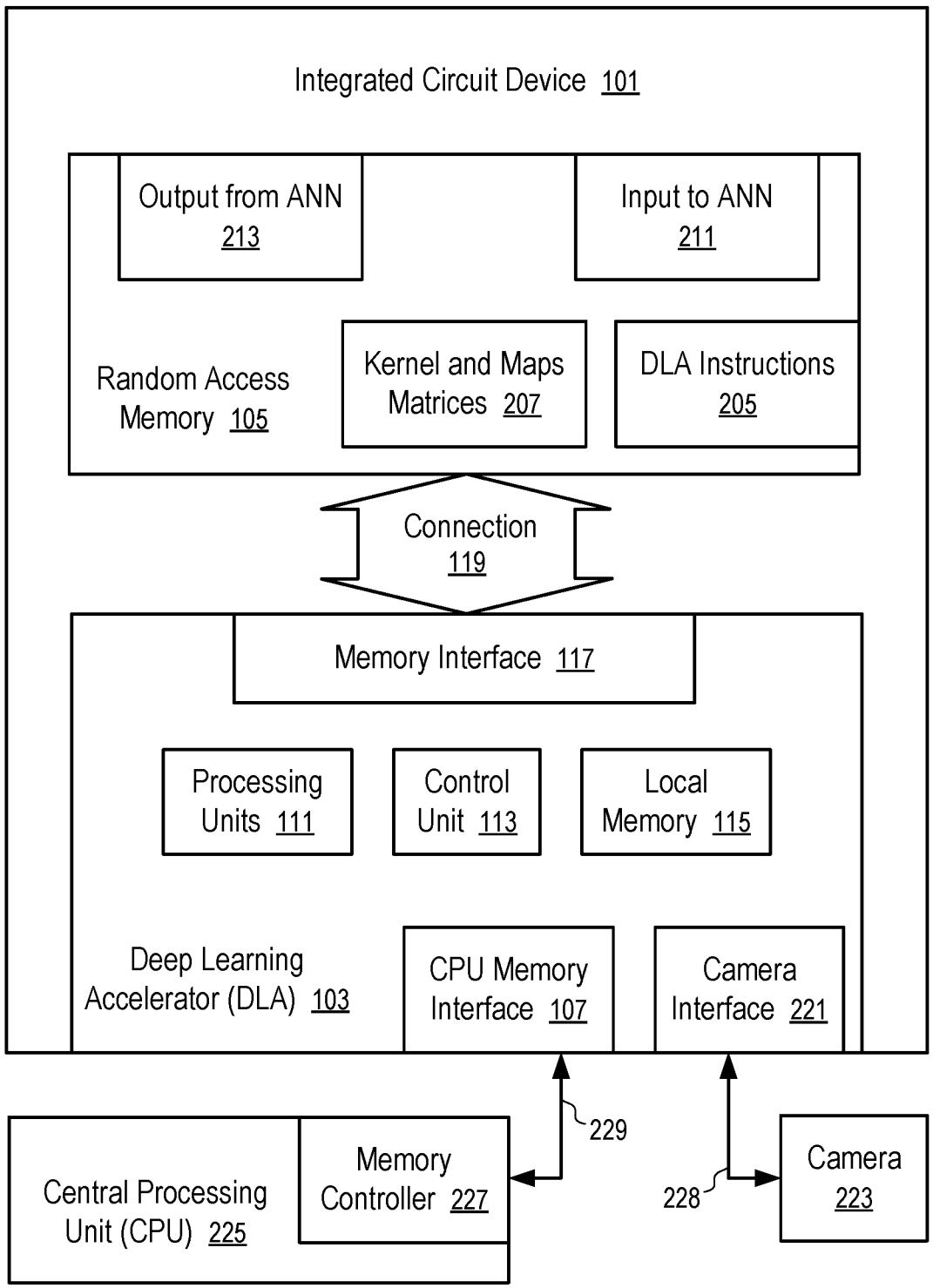
FIG. 7 shows an integrated circuit device having a Deep Learning Accelerator and random access memory with a camera interface according to one embodiment.

FIG. 7 shows an integrated circuit device (101) having a Deep Learning Accelerator (103) and random access memory (105) with a camera interface (221) according to one embodiment.

For example, the Deep Learning Accelerator (103), the random access memory (105), and the connection (119) of the integrated circuit device (101) of FIG. 7 can be configured in a way similar to those illustrated in FIG. 1, FIG. 5, and/or FIG. 6.

The integrated circuit device (101) of FIG. 7 has at least two external interfaces (221 and 107) that can be used concurrently, including a CPU memory interface (107) and a camera interface (221).

The CPU memory interface (107) in the integrated circuit device (101) of FIG. 7 is configured to provide for a connection (229) to a memory controller (227) of a Central Processing Unit (CPU) (225), similar to the CPU memory interface (107) in the integrated circuit device (101) of FIG. 6

In FIG. 7, the CPU memory interface (107) is implemented in the Deep Learning Accelerator (103). For example, the logic circuit of the CPU memory interface (107) can be formed on the integrated circuit die of the Deep Learning Accelerator (103); and the CPU memory interface (107) accesses the random access memory (105) using the memory interface (117) of the Deep Learning Accelerator (103).

Alternatively, the CPU memory interface (107) can be separate from the Deep Learning Accelerator (103) and be implemented in a way as illustrated in FIG. 6. For example, as illustrated in FIG. 6, the CPU memory interface (107) can be configured to access the random access memory (105) using a connection (109) that is separate from the connection (119) between the Deep Learning Accelerator (103) and the random access memory (105). The integrated circuit device (101) of FIG. 6 can also be modified to have the logic circuit of the CPU memory interface (107) and/or the DMA controller interface (106) implemented in the Deep Learning Accelerator (DLA) (103), in a way similar to the CPU memory interface (107) being implemented in the Deep Learning Accelerator (103) of FIG. 7.

The camera interface (221) in the integrated circuit device (101) of FIG. 7 is configured to provide a connection (228) to one or more devices containing or employing image sensors or image generators, such as a camera (223), radar, lidar, medical imaging equipment, etc.

For example, the connection (228) to the camera (223) can be implemented in accordance with a standard for a Mobile Industry Processor Interface (MIPI) protocol, including a MIPI Camera Serial Interface (CSI) protocol. The connection (228) can be used to control the imaging operations of the camera (223) (or another image generator) and to obtain image data from the camera (223) (or another image generator) as input (211) to the Artificial Neural Network (201). In one embodiment, the connection (228) is a serial bus in accordance with a MIPI CSI-2 standard that supports high-performance applications, including 1080p, 4K, 8K and beyond video, and high-resolution photography.

The camera interface (221) can be used to control the operations of the camera (223) in generating image data. For example, the camera interface (221) can be used to send commands to the camera (223) to adjust the resolution of image data provided by the camera (223). For example, the commands sent via the camera interface (221) to the camera (223) can adjust the frame rate and/or exposure time of image data provided by the camera (223). For example, the Deep Learning Accelerator (DLA) (103) can use the camera interface (221) to start or stop the operations of the camera (223) in capturing and/or transferring images.

In some implementations, the camera interface (221) can be used to optionally issue commands to digitally zoom in an area of an interest and thus reduce the amount of data to be transferred over the connection (228) and the amount of computation to be performed by the integrated circuit device (101) on the image data received from the camera (223).

In some implementations, the camera interface (221) can be used to optionally issue commands to adjust the view point and/or field of view of the camera (223).

FIG. 7 illustrates an implementation in which the camera interface (221) is configured in the Deep Learning Accelerator (103). For example, at least a portion of the logic circuit of the camera interface (221) is formed on the integrated circuit die of the Deep Learning Accelerator (103); and the camera interface (107) can access the random access memory (105) using the memory interface (117) of the Deep Learning Accelerator (103).

For example, the camera interface (221) can receive image from the camera (223) through the connection (228) and buffers the image data in the random access memory (105) as input (211) to the Artificial Neural Network (201).

Once the integrated circuit device (101) obtains a set of image data as the input (211), the Deep Learning Accelerator (103) can execute the instructions (205) to generate the output (213), in a way similar to the device of FIG. 1, FIG. 5, and/or FIG. 6.

The instructions (205) can optionally include instructions for the control unit (113) to operate the camera interface (221) and obtain image data, from the camera (223) via the connection (228) through the camera interface (221), as the input (211) to the Artificial Neural Network (201).

In FIG. 7, the camera interface (221) is configured in the Deep Learning Accelerator (103). Alternatively, the camera interface (221) can be separate from the Deep Learning Accelerator (103) and be configured to access the random access memory (105) using a connection that is separate from the connection (119) between the Deep Learning Accelerator (103) and the random access memory (105), in a way similar to the DMA controller interface (106) being separate from the Deep Learning Accelerator (103) in FIG. 6.

The integrated circuit devices (101) of FIG. 6 and FIG. 7 can be modified to have three external interfaces: a CPU memory interface (107), a DMA controller interface (106), and a camera interface (221). Optionally, the camera interface (221) can include a direct memory access controller to load image data into the random access memory (105) from the camera (223), e.g., in parallel with the Central Processing Unit (225) retrieving output (e.g., 213) from the random access memory (105). The camera interface (221) and the DMA controller interface (106) can optionally share a portion of logic circuit for supporting the operations of direct memory access controllers.

In a method according to one embodiment, an integrated circuit device (101) stores matrices (207) of an Artificial Neural Network (201) and instructions (205). The instructions (205) are executable by at least one processing unit (111) enclosed within the integrated circuit device (101) to implement, using the matrices (207), the computations of the Artificial Neural Network (201). The integrated circuit device (101) has a first interface (107) configured to be connected to a memory controller (227) and a second interface (221) configured to be connected to an image generator, such as a camera (223), radar, lidar, ultrasound scanner, or medical imaging equipment.

For example, the second interface (221) implements a camera command interface protocol, and/or a Mobile Industry Processor Interface (MIPI) protocol. For example, the second interface (221) is configured to be connected to a camera (223) via a serial bus connection (228) in accordance with a Mobile Industry Processor Interface (MIPI) Camera Serial Interface (CSI) protocol.

The integrated circuit device (101) communicates, via the second interface (221), with the image generator (e.g., 223) to receive image data as input (221) to the Artificial Neural Network (201).

The integrated circuit device (101) executes the instructions (205) to generate output (213) from the Artificial Neural Network (201) according to the input (211).

The integrated circuit device (101) stores, in random access memory (105) that is enclosed within the integrated circuit device (101), the output (213) from the Artificial Neural Network (201).

The integrated circuit device (101) provides, via the first interface (107), the output (213) to a Central Processing Unit (225) that is in control of the memory controller (227).

For example, the integrated circuit device (101) can buffer, into the random access memory (105) via the second interface (221) and as input to the Artificial Neural Network (201), a next set of image data from the image generator (e.g., 223), while simultaneously providing, from the random access memory (105) via the first interface (107) and concurrently with the buffering, output previously generated from the Artificial Neural Network (201) according to a prior set of image data from the image generator (e.g., 223).

For example, the integrated circuit device (101) can be enclosed within an integrated circuit package. The integrated circuit device (101) has a Deep Learning Accelerator (103) with processing units (111), a control unit (113) and local memory (115). The processing units (111) include at least a matrix-matrix unit (121) configured to execute an instruction having two matrix operands; the matrix-matrix unit (121) includes a plurality of matrix-vector units (141 to 143) configured to operate in parallel; each of the matrix-vector units includes a plurality of vector-vector units (161 to 163) configured to operate in parallel; and each of the vector-vector units includes a plurality of multiply-accumulate units (171 to 173) configured to operate in parallel.

For example, the integrated circuit device (101) can transmit, via the second interface (221), a command to the image generator (e.g., 223), where the command instructs the image generator (e.g., 223) to adjust resolution or frame rate of image data generated by the image generator (e.g., 223).

For example, the integrated circuit device (101) can transmit, via the second interface (221), another command to the image generator (e.g., 223) to instruct the image generator (e.g., 223) to adjust an area of interest, a point of view, or a field of view of image data generated by the image generator (e.g., 223).

Figure 8:
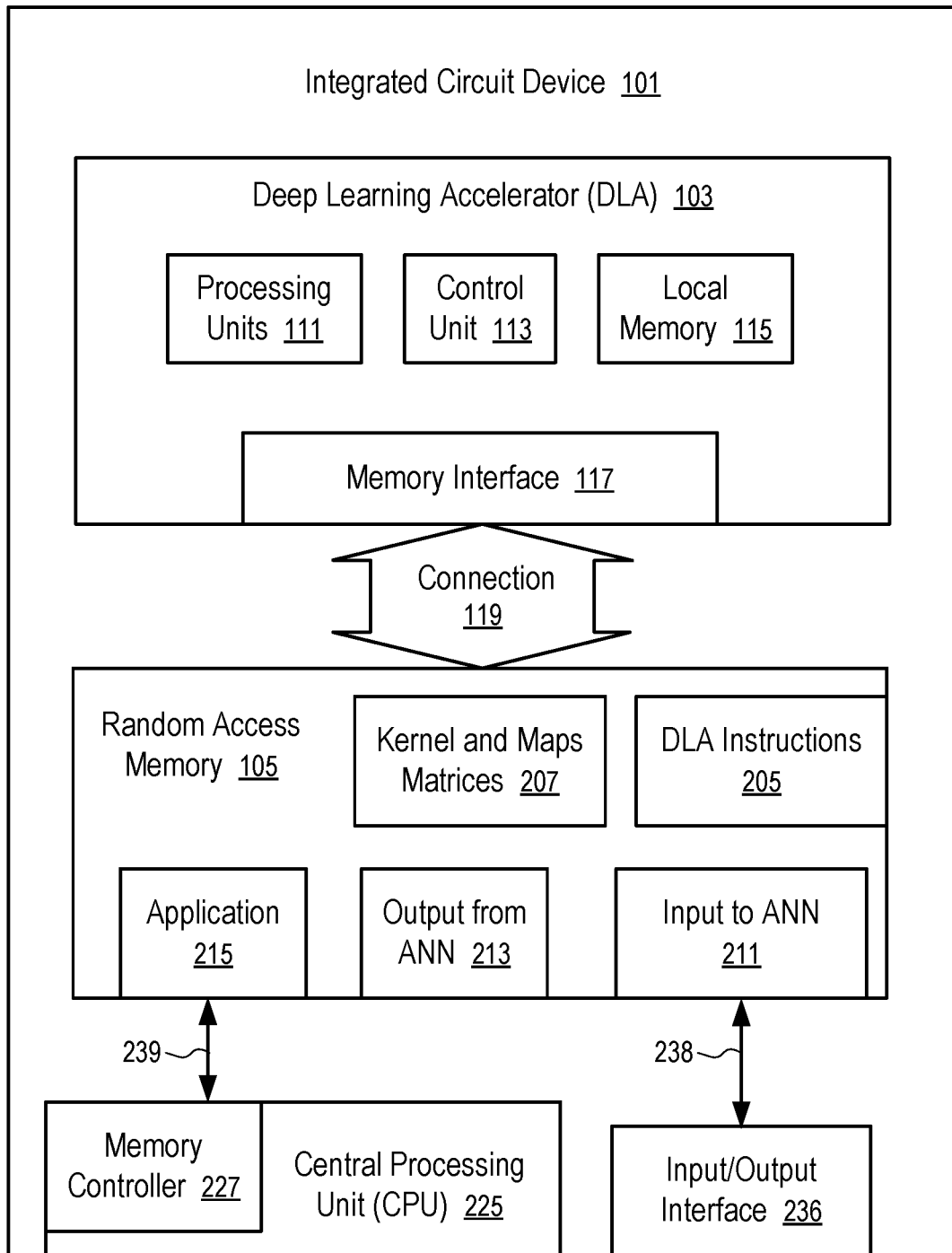
FIG. 8 shows a system on a chip according to one embodiment.

FIG. 8 shows a system on a chip according to one embodiment.

The system of FIG. 8 is packaged in an integrated circuit device (101). The integrated circuit device (101) of FIG. 8 has a Deep Learning Accelerator (103), random access memory (105), and a connection (119) between the Deep Learning Accelerator (103) and random access memory (105), which can be configured a way similar to those illustrated in FIG. 1, FIG. 5, FIG. 6, and/or FIG. 7.

The integrated circuit device (101) of FIG. 8 further includes a Central Processing Unit (CPU) (225). The Central Processing Unit (CPU) (225) can have one or more processing cores. When the Central Processing Unit (CPU) (225) has more than one processing cores, multiple processing cores of the Central Processing Unit (CPU) (225) can operate independent from each other and operate in parallel.

The Central Processing Unit (225) has a memory controller (227). A connection (239) is provided in the integrated circuit device (101) between the memory controller (227) and the random access memory (105). For example, the integrated circuit package of the device (101) can include a substrate to support the integrated circuit dies enclosed therein. The substrate can provide connections (239, 238, 119) among components within the integrated circuit device (101), such as the Central Processing Unit (225), the random access memory (105), the Deep Learning Accelerator (103), and/or the input/output interface (236). For example, an interposer can be affixed to the substrate to provide the connections (e.g., 239, 238, 119) and/or connections to the connectors (e.g., pins or solder balls) of the integrated circuit device (101).

A portion of the random access memory (105) can be reserved for use by the Central Processing Unit (225) and thus not used by the Deep Learning Accelerator (103). Such a portion can be used to store the instructions of an application (215) and/or an operating system that are programmed to be executed by the Central Processing Unit (225). Logical memory allocated and used during the execution of the application (215) can be mapped, by the memory controller (227) and/or an operating system executed by the Central Processing Unit (225), to the physical memory in the portion of the random access memory (105) reserved for the Central Processing Unit (225).

Another portion of the random access memory (105) can be shared between the Central Processing Unit (225) and the Deep Learning Accelerator (103). The Deep Learning Accelerator (103) can write the output (213) from the Artificial Neural Network (201) to the shared portion; and the Central Processing Unit (225) can read the output (213) from the shared portion as input to the application (215) running/executed in the Central Processing Unit (225). For example, the shared portion configured for the output (213) can be read only for the Central Processing Unit (225) and write only for the Deep Learning Accelerator (103).

A further portion of the random access memory (105) can be used to buffer input (211) to the Artificial Neural Network (201) that is represented and/or implemented by the DLA instructions (205) and the matrices (207).

The integrated circuit device (101) has an input/output interface (236) that can be used to receive sensor data from one or more sensors, such as an image sensor, a microphone, etc. The received sensor data can be stored into the buffer portion of the random access memory (105) as the input (211) to the Artificial Neural Network (201).

For example, the input/output interface (236) can be an interface to a peripheral bus, such as a Universal Serial Bus (USB), a Serial Advanced Technology Attachment (SATA) bus, a Peripheral Component Interconnect express (PCIe) bus, a Small Computer System Interface (SCSI) bus, a Fibre Channel, a Serial Attached SCSI (SAS) bus, or any other bus.

For example, the input/output interface (236) can be a camera interface (221), e.g., as illustrated in FIG. 7 and configured to receive image data from a camera or an image generator.

For example, the input/output interface (236) can be a direct memory access controller interface (106), e.g., as illustrated in FIG. 6 and configured to receive sensor data from a direct memory access controller.

The Central Processing Unit (225) and/or the Deep Learning Accelerator (103) can use the input/output interface (236) to control the operation of a sensor configured on the bus and to receive sensor data from the sensor.

Additional external devices can be connected to the bus accessible to the input/output interface (236). Such devices can include a communication device configured to communicated over a wired or wireless computer connection, such as a wired or wireless local area network, a wireless personal area network, a wireless wide area network, a cellular communications network, and/or the Internet. Such devices can also include a display device, a monitor, a touch screen, a speaker, a keyboard, a mouse, a touch pad, and/or a track ball, etc. to present a user interface of the application (215). Through the input/output interface (236), the application (215) executed in the Central Processing Unit (225) can access the devices connected on the bus.

The input/output interface (236) has a connection (238) to the input portion of the random access memory (105). The connection (238) can be used to load input (211) into the random access memory (105) (e.g., from a sensor device) in parallel with the Central Processing Unit (225) accessing the random access memory (105) in reading the output (213) and/or executing the application (215).

The Central Processing Unit (225) and the Deep Learning Accelerator (103) can be formed on separate integrated circuit dies. For example, the Deep Learning Accelerator (103) can be formed on an integrated circuit die stacked above one or more integrated circuit dies of the random access memory (105); and the Central Processing Unit (225) can be formed on a further integrated circuit die stacked below the one or more integrated circuit dies of the random access memory (105). Optionally, a portion of the random access memory (105) reserved for the Central Processing Unit (225) can be configured on a further integrated circuit die stacked under the Central Processing Unit (225). The integrated circuit dies can be connected using Through-Silicon Vias to provide the connections (119 and 239).

Alternatively, when the integrated circuit dies of the Central Processing Unit (225) and the Deep Learning Accelerator (103) are smaller in size than the integrated circuit die of the random access memory (105), both the Central Processing Unit (225) and the Deep Learning Accelerator (103) can be stacked above (or under) the integrated circuit die of the random access memory (105).

Alternatively, an integrated circuit die is configured with wires to provide connections; and the integrated circuit die with the wires is used as a substrate to support integrated circuit dies of the Central Processing Unit (225), the Deep Learning Accelerator (103), and the random access memory (105). Through-Silicon Vias (TSVs) from the substrate integrated circuit die to the other integrated circuit dies stacked on it (and/or underneath it) can be used to provide the connections (119, 239, and/or 238). Optionally, the signal processing circuit of the input/output interface (236) is configured in the substrate integrated circuit die.

In some implementations, the random access memory (105) includes non-volatile memory configured to store the matrices (207) of the Artificial Neural Network (201) and the instructions (205) for the Deep Learning Accelerator (103). For example, such non-volatile memory can be configured in an integrated circuit die stacked above the Deep Learning Accelerator (103).

Alternatively, the Deep Learning Accelerator (103) and the Central Processing Unit (225) can be configured on a same integrated circuit die. The Deep Learning Accelerator (103) and the Central Processing Unit (225) can optionally share circuit and connections for the memory interface (117) and the memory controller (227). Further, the Deep Learning Accelerator (103) and the Central Processing Unit (225) can share a portion logic circuit configured for loading instructions from the random access memory (105). In some implementations, the matrix/vector processing units (111) of the Deep Learning Accelerator (103) are configured as matrix/vector execution units of the Central Processing Unit (225).

For example, the Central Processing Unit (225) can have logic circuit configured to load instructions (e.g., 215 and/or 205) from the random access memory (105) for execution. Matrix/vector instructions are dispatched to processing units (111); and other instructions are dispatched to the Arithmetic-Logic Units (ALUs) of the Central Processing Unit (225) for execution. The processing units (111) can have additional circuits to load matrix/vector operands from the random access memory (105) and/or store results to the random access memory (105). Thus, the Deep Learning Accelerator (103) and the Central Processing Unit (225) can cooperated with each other in executing the instructions (205) of the Artificial Neural Network (201).

In a method according to one embodiment, a Deep Learning Accelerator (103) and a Central Processing Unit (225) can operate substantially independent from each other. The Deep Learning Accelerator (103) generates inference results from sensor data according to an Artificial Neural Network; and the Central Processing Unit (225) runs an application that may use inference results from the Artificial Neural Network. The inference results can be updated periodically based on the incoming stream of sensor data; and the application running the Central Processing Unit (225) can use the inferences results generated from previously received sensor data.

In the method, the integrated circuit device (101) stores, in its random access memory (105), matrices (207) of an Artificial Neural Network (201) and first instructions (205) that are executable by at least one processing unit (111) enclosed within the integrated circuit device (101) to implement the Artificial Neural Network (201) using the matrices (207).

Through an interface (236) to a bus that is external to the integrated circuit device (101), sensor data is loaded into the random access memory (105) as input (211) to the Artificial Neural Network (201).

The at least one processing unit (111) executes the first instructions (205) to generate output (215) from the Artificial Neural Network (201) based on the input (211).

The integrated circuit device (101) stores, in the random access memory (105), the output (213) from the Artificial Neural Network (201).

Operations of the Deep Learning Accelerator (103) can be repeated for multiple sets of input (211) corresponding to sensor data generated in different time windows. After a predetermined number of sets of output (213) are stored in the random access memory (105), the oldest can be may be overwritten to store the newest set.

In some implementations, loading the next set of sensor data into the random access memory (105) and/or storing the output generated from the previously set of sensor data into the random access memory (105) can be performed in parallel with executing the first instructions (205) to generate output from the current set of sensor data.

Further, in the method, the integrated circuit device (101) stores, in its random access memory (105), second instructions of at least one application (215) programmed for execution by a Central Processing Unit (225) enclosed within the integrated circuit device (101).

The Central Processing Unit (225) executes the second instructions of the at least one application (215) that uses output (213) from the Artificial Neural Network (201).

The Central Processing Unit (225) reads, from the random access memory (105), output (213) from the Artificial Neural Network (201).

The Central Processing Unit (225) processes the output (213) in execution of the at least one application (215).

The operations of the Central Processing Unit (225) can be repeated for multiple sets of output (213) that are inference results corresponding to sensor data generated in different time windows.

Optionally, the Central Processing Unit (225) can provide an indication to cause the Deep Learning Accelerator (103) to start or stop generation of new sets of output (213) from the Artificial Neural Network (201).

Optionally, during execution of the first instructions (205), the Deep Learning Accelerator (103) can call a routine to be executed in the Central Processing Unit (225). For example, such a routine can be provided in an operating system executed by the Central Processing Unit (225), or in the application (215) or another application. For example, such a routine can provide a service that does not involve two matrix/vector operands and/or that is suitable for execution in the Arithmetic-Logic Unit (ALU) of the Central Processing Unit (225). Signal lines can be configured between the Deep Learning Accelerator (103) and the Central Processing Unit (225) to facilitate such calls.

In some implementations, the integrated circuit device (101) has multiple stacked integrated circuit dies that are connected using Through-Silicon Vias (TSVs).

For example, the Deep Learning Accelerator (103) can be configured on a first integrated circuit die having the at least one processing unit (111), a control unit (113), local memory (115) configured to store matrix operands for the processing unit(s) (111), and a memory interface (117) to the random access memory (105). The random access memory (105) can be configured on at least one second integrated circuit die.

The Central Processing Unit (225) can be configured on a third integrated circuit die. The at least one second integrated circuit die of the random access memory (105) can be stacked between the first integrated circuit die and the second integrated circuit die. The memory interface (117) of the Deep Learning Accelerator (103) and the memory controller (227) of the Central Processing Unit (225) can be connected to the at least one second integrated circuit die of the random access memory (105) by using separate sets of Through-Silicon Vias (TSVs).

Alternatively, the Central Processing Unit (225) can be configured on the first integrated circuit of the Deep Learning Accelerator (103); and the memory controller (227) of the Central Processing Unit (225) and the memory interface (117) of the Deep Learning Accelerator (103) can share an interface to the random access memory (105) and/or share a logic circuit to load instructions (205 and 215) from the random access memory (105).

In some implementations, a fourth integrated circuit die is configured with wires. The Deep Learning Accelerator (103) in the first integrated circuit die, the random access memory (105) in the at least second integrated circuit die, and/or the Central Processing Unit (225) in the third integrated circuit die (or in the first integrated circuit die) can be connected using the wires in the fourth integrated circuit die and using Through-Silicon Vias (TSVs) from the fourth integrated circuit die to the other integrated circuit dies. Separate sets of Through-Silicon Vias (TSVs) can be connected from the wires in the fourth integrated circuit die and respective integrated circuit dies of the Central Processing Unit (225), the Deep Learning Accelerator (103), and the random access memory (105).

Optionally, a circuit of the interface (236) of the integrated circuit device (101) is also configured on the fourth integrated circuit die to process signals to or from the bus. For example, the bus can be implemented in accordance with a protocol of Universal Serial Bus (USB), Serial Advanced Technology Attachment (SATA) bus, or Peripheral Component Interconnect express (PCIe) for a connection to one or more sensor devices, such as a camera, a microphone, an image generator, etc.

The integrated circuit devices (101) of FIGS. 1 and/or 6-8 can be used to implement edge servers as further discussed below.

Figure 9:
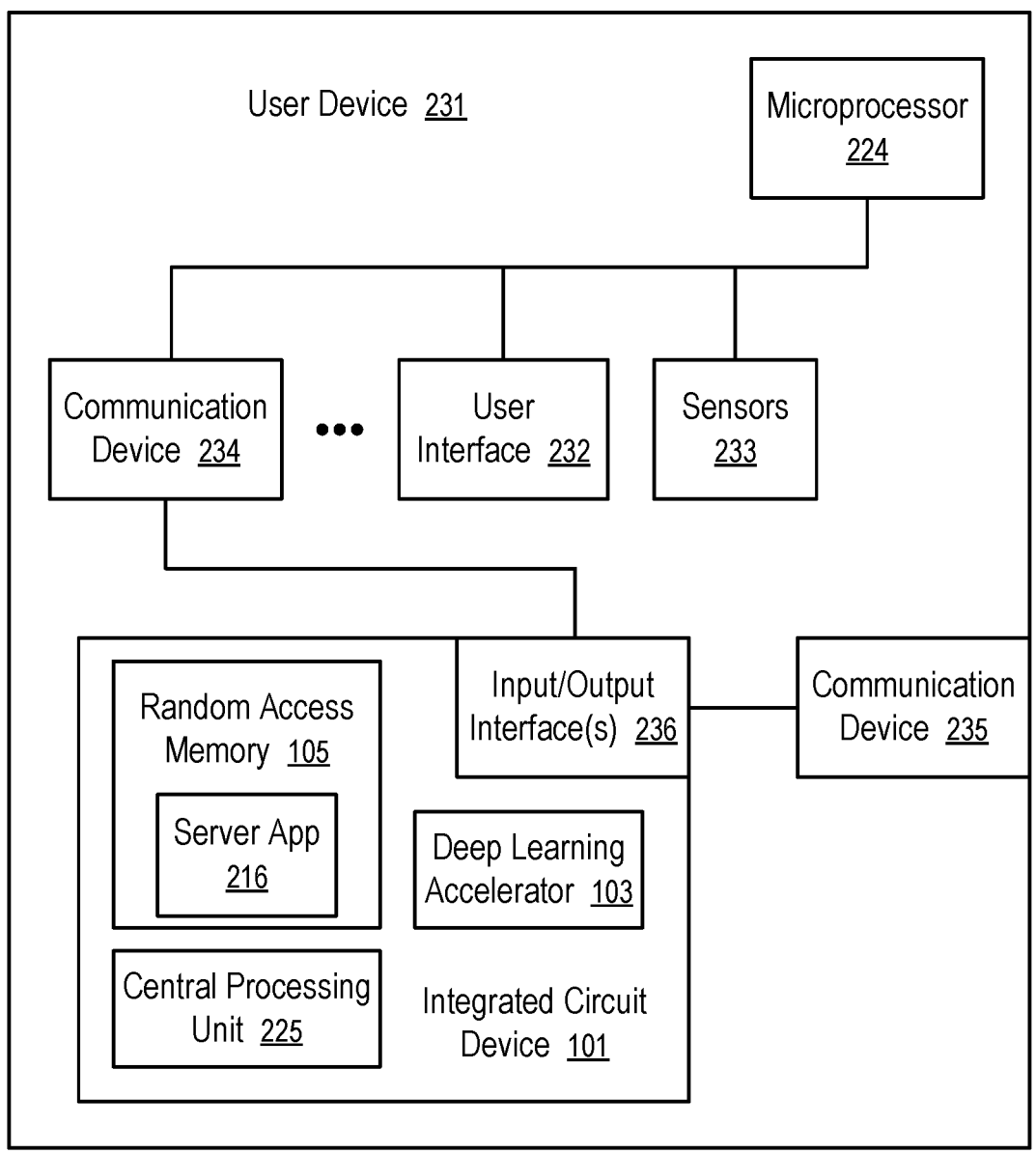
FIG. 9 shows a user device configured with an edge server according to one embodiment.

FIG. 9 shows a user device (231) configured with an edge server according to one embodiment. For example, the edge server illustrated in FIG. 9 can be implemented using the integrated circuit device (101) of FIG. 8.

In FIG. 9, the random access memory (105) of the integrated circuit device (101) stores the instructions of a server application (216). The Central Processing Unit (225) of the integrated circuit device (101) executes the instructions of the server application (216) to provide services to the user device (231).

The user device (231) illustrated in FIG. 9 has a microprocessor (224), sensors (223), a user interface (232), communication devices (234 and 235), and the integrated circuit device (101). The integrated circuit device (101) is used to implement an edge server by running the server application (216) in the Central Processing Unit (225).

For example, the user device (231) can be a mobile device, such as a smart phone, an autonomous vehicle, a security camera, etc. The user device (231) can optionally have multiple sub-systems that have sensor data generators, such as image sensors, microphones, etc. The sensor data generators can provide their sensor data to the integrated circuit device (101) for processing using one or more Artificial Neural Networks.

The user device (231) uses the sensors (232) and/or user interface (232) to generate input data. The input data is stored, through the communication device (234) and the input/output interface(s) (236), into the random access memory (105) as the input (211) to the Artificial Neural Network (201).

The output (213) from the Artificial Neural Network (201) can be provided to an application running in the microprocessor (224) via the input/output interface(s) (236) and the communication device (234). For example, an application running in the microprocessor (224) can query the server application (215) running in the Central Processing Unit (225) for the identifications/classifications of features or events recognized from the input (211).

Additionally or alternatively, the output (213) from the Artificial Neural Network (201) can be provided to a remote server/cloud via the input/output interface(s) (236) and the communication device (235). For example, the communication connection from the communication device (235) can include a cellular communications network and/or the Internet. For example, the communication device (235) can be a modem, a radio or Radio Frequency (RF) chain, a transceiver for wired or wireless communications.

For example, the output (213) can be provided to the remote server/cloud to enable a server application that may or may not provide directly response to the input from the user device (231).

For example, the application running in the microprocessor (224) can query the server application (216) running in the edge server implemented in the integrated circuit device (101). In some instances, the server application (216) can provide a response to the query based on the output (213); and the server application (216) does not have to further communicate with the remote server/cloud for a response to the query. In other instances, the server application (216) leverages the remote server/cloud in generating a response to the query. Thus, the server application (216) provides the output (213) to the remote server/cloud to request for a response to the query from the application running in the microprocessor (224). When the output (213) is sufficient to generate the response, the server application (216) can forward the response to the application running in the microprocessor (224). When the remote server/cloud determines that the output (213) is insufficient and the input (211) is to be further processed to generate the response to the query, the remote server/cloud can request the server application (216) to transmit the server application (216) to the server application (216).

In some implementations, the communications and/or cooperation between the server application (216) and the remote server/cloud may not be driven by requests or queries from the microprocessor (224). For example, the edge server and the remote server/cloud can be configured to monitor the events and/or surroundings of the user device (231) to generate alert, notification, and/or instructions for the user device (231) or another device. When the output (213) stored by the deep learning accelerator (103) in the random access memory (105) includes successful identification of an event, an object, or an feature, the server application (216) and/or the remote server/cloud can process the identified event, object, and/or feature without further communicating the input (211) from the integrated circuit device (101) to the remote server/cloud. Otherwise, the integrated circuit device (101) can optionally transmit the input (211) to the remote server/cloud for further analysis.

FIG. 9 illustrates an example of using separate communication devices (234 and 235) for communicating with the microprocessor (224) and for communicating with a remote server/cloud. Optionally, a same communication device can be shared in communicating with the microprocessor (224) and in communicating with a remote server/cloud through a same network interface.

Further, in some instances, the input (211) to the Artificial Neural Network can includes data received via the communication device (235) from other devices in a local area. For example, the user device (231) can be a hub of Internet of Things in a house or a building. For example, the user device (231) can be a router, an access point, or a base station configured in or near a house, a building, or a business.

FIG. 9 illustrates an example where an edge server is implemented using an integrated circuit device (101) similar to that of FIG. 8 in having a Central Processing Unit (225). Alternatively, the integrated circuit device (101) similar to that of FIG. 7 can be used, where the microprocessor (224) can function as a Central Processing Unit (224).

In another alternative implementation, the Central Processing Unit (225) of the integrated circuit device (101) can be used to replace the microprocessor (224). Thus, the user device (231) can be configured to run its applications (e.g., 215) using the processing power of the Central Processing Unit (225) of the integrated circuit device (101); and the microprocessor (224) can be eliminated.

Figure 10:
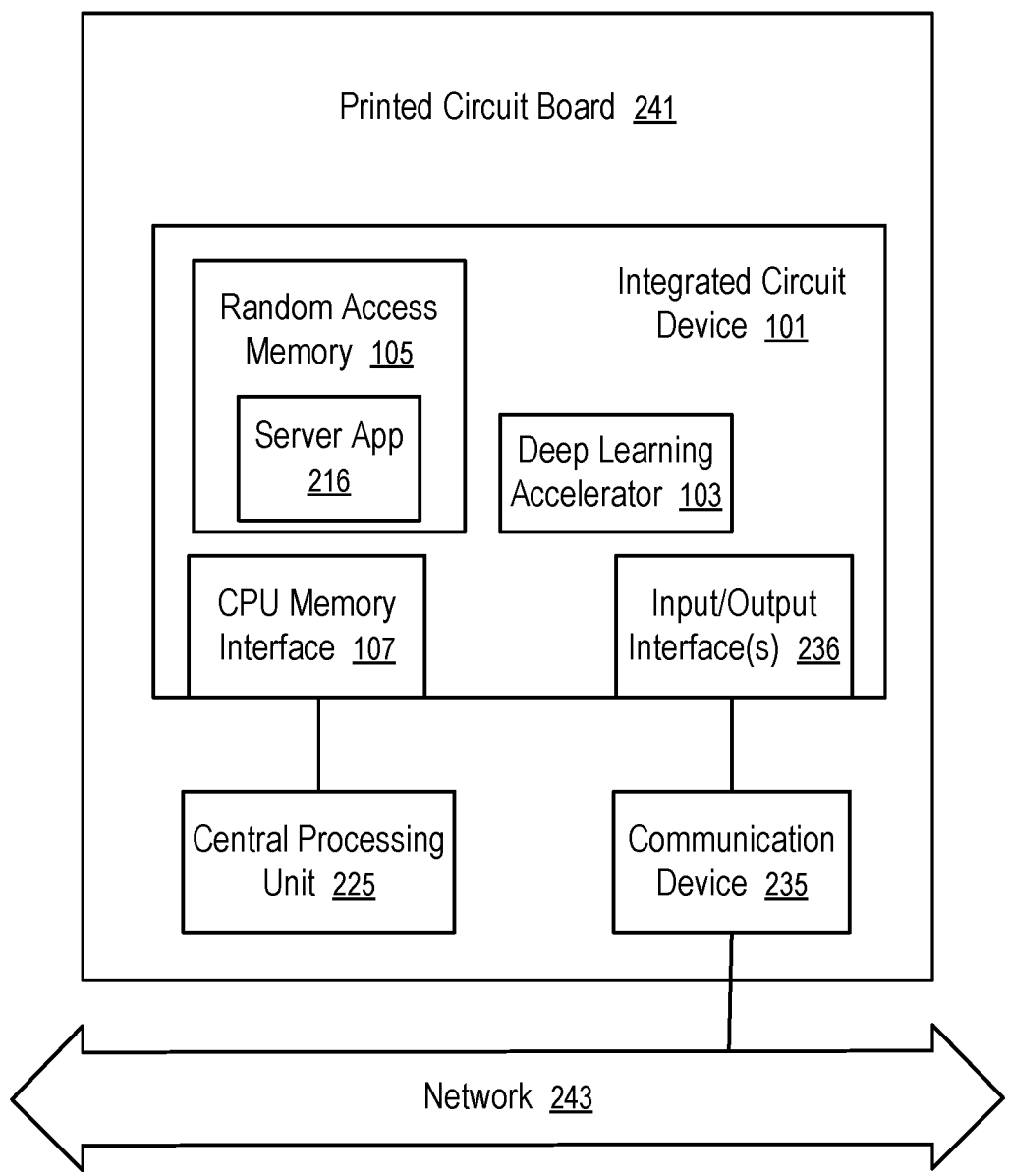
FIG. 10 shows an edge server implemented according to one embodiment.

FIG. 10 shows an edge server implemented according to one embodiment.

In FIG. 10, an edge server is configured on a printed circuit board (241) with an integrated circuit device (101) similar to that of FIG. 7 in having a CPU memory interface (107). A Central Processing Unit (225) configured on the printed circuit board (241) is connected to the CPU memory interface (107) to run a server application (216).

Alternatively, the combination of the Central Processing Unit (225) and the integrated circuit device (101) of FIG. 7 can be replaced with an integrated circuit device (101) of FIG. 8 that includes a Central Processing Unit (225).

Alternatively, the Central Processing Unit (225) can be replaced with an interface to a memory bus or a peripheral bus of a computer system. Thus, the existing microprocessor or Central Processing Unit (225) of the computer system can be used to run the server application (216) in the random access memory (105).

The edge server of FIG. 10 includes a communication device (235) configured to communicate with other devices through a computer network (243). For example, the network (243) can be a local area network, a wireless local area network (e.g., WiFi), or a wireless personal area network (e.g., Bluetooth). The network (243) can be connected to local user devices (e.g., 231) to receive sensor data. The network (243) can be further connected to a remote server/cloud via an internet service provider, a telecommunications network, a cellular communications network, etc.

The edge server of FIG. 10 can be added to a local computer network to function as a proxy of a remote server/cloud, such that a portion of data intensive computation can be performed at the local computer network to generate the output from an Artificial Neural Network.

In a method according to one embodiment, an edge server illustrated in FIG. 9 and/or FIG. 10 is configured to process sensor data in a local area as a proxy of a remote, centralized server.

In the method, the edge server stores, in random access memory (105) configured in an integrated circuit device (101), matrices (207) of an Artificial Neural Network (201), first instructions (205) executable by at least one processing unit (111) enclosed within the integrated circuit device (101), and second instructions of a server application (216) programmed for execution by a Central Processing Unit (225). The first instructions (205) can be executed by the least one processing unit (111) to implement the Artificial Neural Network (201) using the matrices (207).

Optionally, the Central Processing Unit (225) can be configured in the integrated circuit device (101), as illustrated in FIGS. 8 and 9.

The edge server loads data into the random access memory (105) as input (211) to the Artificial Neural Network (201).

For example, the edge server can receive from a wired or wireless local area network, a wireless personal area network, a peripheral bus, or a memory bus, the data from sensors (233) of one or more user devices (231); and the data can be stored in the random access memory (105) as the input (211) to the Artificial Neural Network (201).

For example, the edge server can include a communication device (235) that is configured to communicate with the one or more user devices (231) using a protocol of local area network, wireless local area network, or wireless personal area network to obtain the sensor data.

The at least one processing unit (111) executes the first instructions (205) to generate output (213) from the Artificial Neural Network (201) responsive to the input (211).

The edge server stores, into the random access memory (105), the output (213) from the Artificial Neural Network (201).

The Central Processing Unit (225) executes the second instructions of the server application (216) to provide, based on the output (213), services over a computer network (243).

For example, the edge server can provide the services as a proxy of a remote computer system configured on the Internet. For example, the remote computer system can be a centralized server, or a cloud computing infrastructure. The edge server can communicate with the remote computer system over a telecommunications network, a cellular communications network, or the Internet, or any combination thereof.

For example, the edge server can be configured in an apparatus having circuitry of a network interface card, a router, a hub of Internet of Things, an access point of a wireless computer network, or a base station of a cellular communications network, or any combination thereof. Since such an apparatus is close to user devices (231), the computation of the edge server in processing the sensor data can take place at a network location close to the source of the sensor data. Thus, the data transmission latency can be reduced. For example, the communication device (235) of the edge server can be coupled to the networking circuitry of the apparatus to provide services between local user devices (231) and the remote computer system. In some implementations, the edge server is configured on a separate integrated circuit board (241) so that the edge server can be added on to the networking apparatus. In other implementations, the edge server can be configured as part of a user device (231). For example, the edge server can be added to the networking apparatus via a computer networking connection port, or to a user device via a bus, such as a bus configured in accordance with a protocol of Universal Serial Bus (USB), Serial Advanced Technology Attachment (SATA) bus, or Peripheral Component Interconnect express (PCIe).

For example, in providing the services, the edge server can transmit the output (213) to the remote computer system and thus avoid or reduce the need to transmit the input (211).

For example, in providing the services, the edge server can transmit the data from the local user device(s) (231) to the remote computer system only when the remote computer system determines that the output (213) is insufficient for a service and thus requests the data from the edge server.

For example, in providing the services, the edge server can provide the output (213) and/or other results to a user device (231) without help from the remote computer system when the output (213) or the other results are determined to be sufficient for the services.

For example, the server application (216) executed in the Central Processing Unit (225) can be configured to generate an alert, a notification, or a response to a query, or any combination thereof based on the output (213), such as an identification of an event, an object, a feature, etc.

Edge servers illustrated in FIG. 9 and FIG. 10 can be used to monitor a patient as further discussed below.

Figure 11:
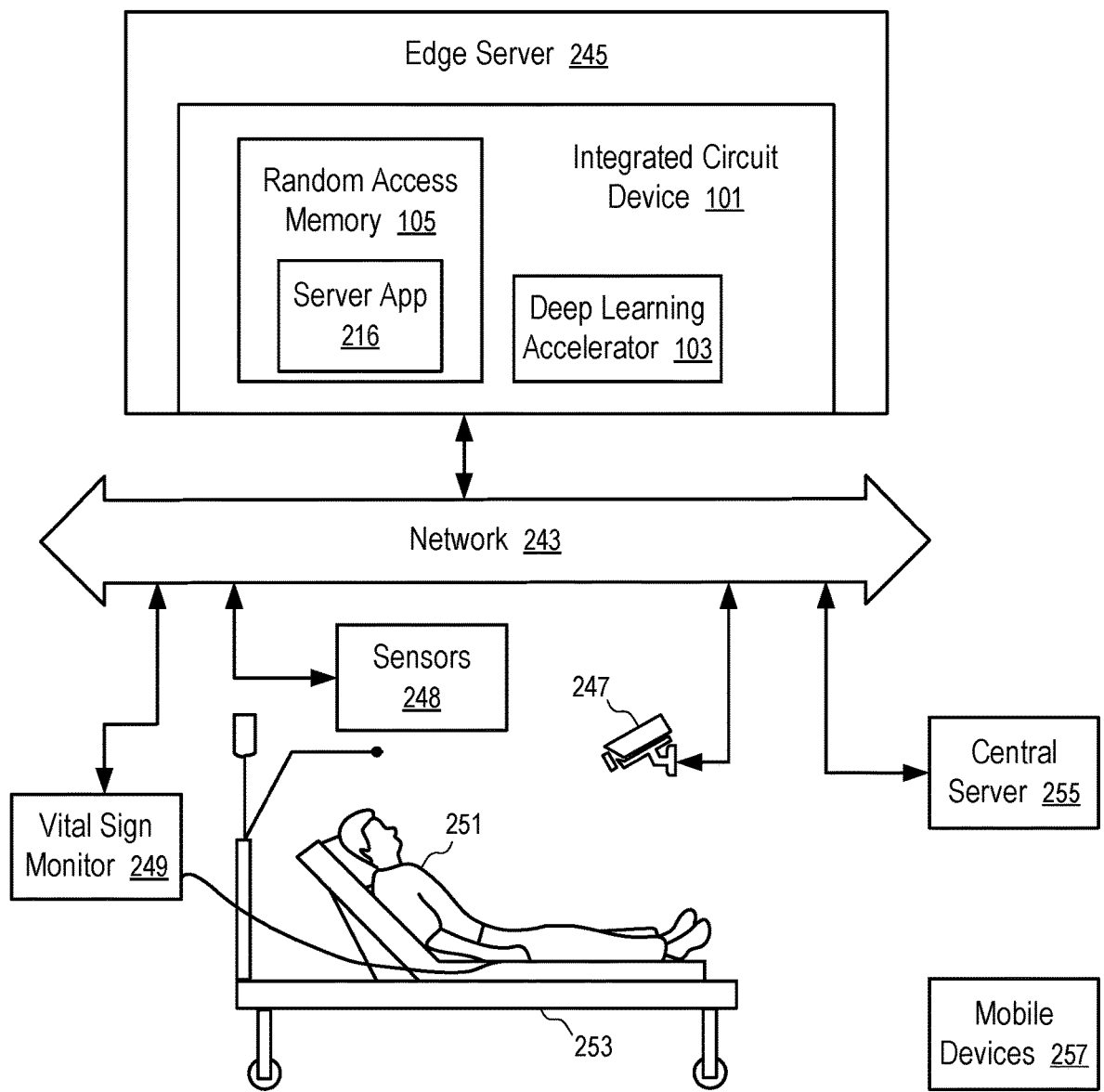
FIG. 11 shows a system configured to monitor a patient according to one embodiment.

FIG. 11 shows a system configured to monitor a patient (251) according to one embodiment.

In the system of FIG. 11, medical devices and sensors (e.g., 247, 248, and 249) are configured to collect real-time information about a patient (251) being monitored in a hospital or a care center, or at home or another location.

The patient (251) may be in a bed (253) and may not be able to self-report troubles and/or dangerous developments, such as falling out of the bed, acute worsening of a disease, failing of an internal organ, difficulties with a body function, etc. The system of FIG. 11 can be used to monitor the condition of the patient (251) and request assistance when troubles are detected and/or predicted.

For example, the medical devices and sensors used to monitor the patient can include a camera (247) monitoring the visual and/or audio impression of the patient (251).

For example, a vital sign monitor (249) can be used to obtain the measurement of the body temperature of the patient (251), the blood pressure of the patient (251), the pulse rate of the patient (251), the respiratory rate of the patient (251), the oxygen saturation level of the patient (251), and/or the blood glucose level of the patient (251), etc.

For example, additional sensors (248) can be used to monitor the stress level of the user (e.g., using a galvanic skin sensor), to monitor the muscle activities of the patient (251) (e.g., using an electromyography sensor), to monitor the heart activities of the patient (251) to generate electrocardiogram, etc.

The edge server (245) can be configured to generate alerts at least based on predetermined thresholds for vital signs measured for the patient (251).

For example, when the pulse rate of the patient (251) is outside of a predetermined range, the edge server (245) can generate an alert to a caretaker, a nurse, and/or a medical doctor. For example, the edge server (245) can transmit the alert to a central server (255) with an identification of the patient (251); and the central server (255) can be configured to identify the mobile device(s) (257) of the caretaker, the nurse, and/or the medical doctor who are currently assigned to process the alert, and further transmit the alert to the mobile device(s) (257).

In some instances, the threshold-based alerts can be less accurate in detecting and/or predicting an urgent development that requires intervention by a caretaker, a nurse, and/or a medical doctor. The development of a situation that requires intervention can be predicted in many situations from a pattern in the data generated by the medical devices and sensors (e.g., 247, 248, and/or 249), as may be predicted by an experienced medical practitioner. The prediction can provide valuable time and information for the preparation of the intervention.

The edge server (245) can be configured with an Artificial Neural Network (201) trained to recognize patterns in the data collected by the devices and sensors (e.g., 247, 248, and 249). When a pattern leading to an known situation that requires intervention is detected, the Artificial Neural Network (201) can generate an estimate of the expected time to the occurrence of the situation, the probability of the occurrence, and/or the severity level of the situation. The prediction can be made based at least in part the medical history of the patient (251). The inference results from the Artificial Neural Network (201) can be used in a dispatch system of the central server (255) in prioritizing resources in handling possible situations in a population of patients (e.g., 251).

The edge server (245) can be connected to communicate with the medical devices and sensors (e.g., 247, 248, and/or 249) within a wired and/or wireless local area network that is configured in a facility near one or more patients (e.g., 251). Edge servers (e.g., 245) can be connected to a central server (255) at a remote location via a telecommunications network, a wireless wide area network, a cellular communications network, and/or the Internet. The edge server (245) can be implemented in a router or gateway of the local area network to a larger network, such as the Internet. The central server (255) is configured to manage the resources (e.g., caretakers, nurses, and/or medical doctors) for intervention. For example, the central server (255) can identify the mobile devices (257) of caretakers, nurses, and/or medical doctors that are currently in vicinity of the patients and/or available to take actions, schedule their workloads, and transmit alerts with inference results to the mobile devices (257) to prepare for intervention.

The Artificial Neural Network (201) implemented in the edge server (245) and its inference capability can be improved over a period of time through the collection and use of training data obtained during the monitoring of a population of patients (e.g., 251).

For example, the edge server (245) can be configured to store, in its random access memory (105) or another data storage device, input (211) generated by the medical devices and sensors (e.g., 247, 248, and/or 249) in the last period of time of a predetermined length (e.g., 10 minutes, half an hour, or a hour). When a vital sign or another measurement generated by one of the medical devices and sensors (e.g., 247, 248, and/or 249) reaches a threshold (or another condition is reached to request intervention, such as when the patient (251) requests assistance), the edge server (245) can provide the stored input (211) for the latest period of time of the predetermined length to the central server (255) for further analysis.

In some instances, the central server (255) is configured with a more powerful Artificial Neural Network (201) that can diagnose the condition of the patient (251). The diagnosis can be provided with an alert to a mobile device (257) of a caretaker, a nurse and/or a physician to request assistance or intervention.

In some instances, the Artificial Neural Network (201) of the edge server (245) is configured to recognize data patterns of known safe conditions. When a data pattern deviates from the known safe patterns, the edge server (245) can request the central server (255) to perform a diagnosis and/or prediction. When the central server (255) does not recognize the data patterns to be safe, a request is transmitted to one or more computing devices (e.g., 257) to obtain a decision from a professional or expert.

In some implementations, the central server (255) can assist the edge server (245) to reach a diagnosis and/or prediction. For example, the Artificial Neural Network (201) implemented in the edge server (245) can be used to process the input (211) in extracting features that are transmitted to the central server (255) as input to generate a diagnosis and/or prediction. Based on the extracted features, the central server (255) can recognize, in some instances, data patterns in the input (211) that can be used to predict the condition and optionally request the transmission of the input (211). In other instances, the central server (255) may not be able to diagnose the condition of the patient (251); and a diagnosis can be reached after the review by an expert, and/or after the further inspection of the patient (251) and/or further investigation.

For example, during and/or after the processing of an alert, a caretaker, a nurse and/or a physician can diagnose the condition of the patient (251) through reviewing the input (211) and/or inspecting the patient (251). Further, the caretaker, the nurse and/or the physician can rate the severity of the condition as input to the central server (255).

The central server (255) can use the diagnosis input about the patient (251). Further, the diagnosis input from the caretaker, the nurse, the physician, and/or the expert can be used to train the Artificial Neural Network (201) implemented in the edge server (245) by adjusting the parameters in the Artificial Neural Network (201) to reduce the differences between the diagnosis and ratings provided by the Artificial Neural Network (201) and the diagnosis and ratings provided by the caretaker, the nurse, the physician, and/or the expert. For example, the training can be performed using a supervised machine learning technique and/or an unsupervised machine learning technique that can classify data into different patterns or clusters.

Thus, over a period of time, the diagnosis and prediction capability of the Artificial Neural Network (201) can improve to reach and/or exceed the capability of an average caretaker, nurse and/or physician. The edge server (245) can function as a virtual caretaker or nurse in the role of monitoring the condition of a patient (251) to request, call for, and/or arrange assistance and/or intervention in the mitigation of dangerous conditions.

Figure 12:
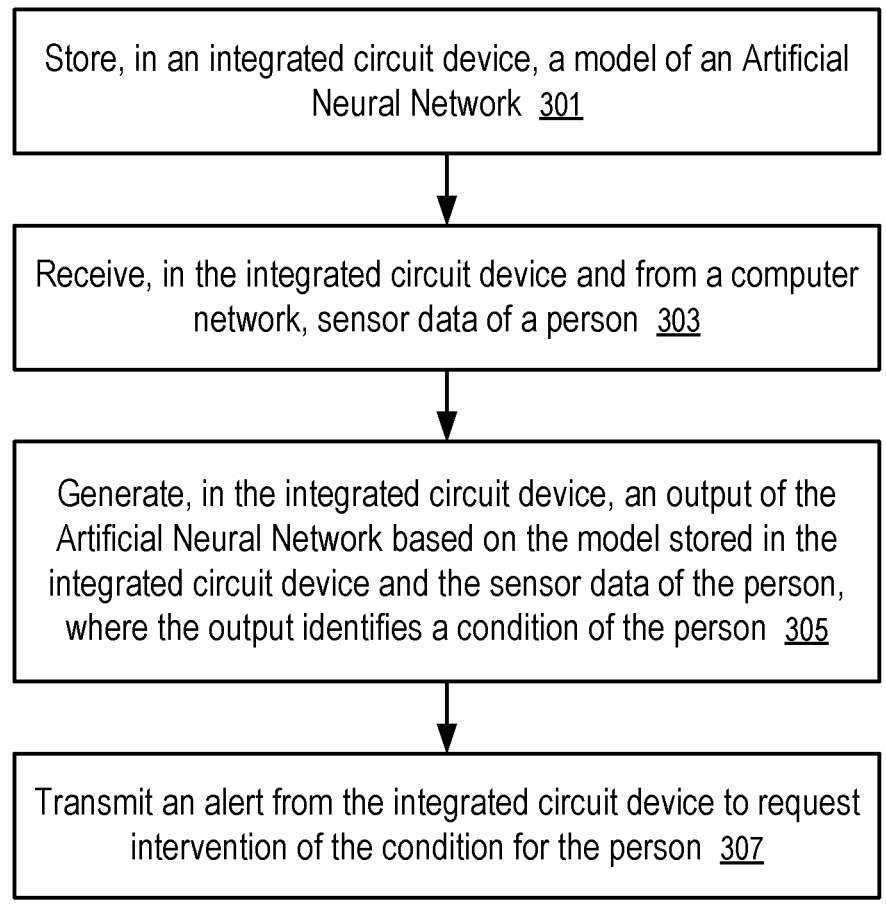
FIG. 12 shows a method of monitoring a patient according to one embodiment.

FIG. 12 shows a method of monitoring a patient according to one embodiment. For example, the method can be implemented in a system illustrated in FIG. 11.

At block 301, an edge server (245) stores, in an integrated circuit device (101), a model of an Artificial Neural Network (201).

For example, the model can be generated by a compiler (203) and can include instructions (205) and matrices (207).

At block 303, the edge server (245) receives, in the integrated circuit device (101) and from a computer network (e.g., 243), sensor data of a person (251).

For example, the edge server (245) can communicate, within a local area network, with sensors (e.g., 247, 248, 249) to receive the sensor data. Examples of the sensors can include a vital sign monitor (249) and a digital camera (247).

At block 305, the edge server (245) generates, in the integrated circuit device (101), an output (213) of the Artificial Neural Network (201) based on the model stored in the integrated circuit device (101) and the sensor data of the person (251), where the output identifies a condition of the person (251).

For example, the output (213) of the Artificial Neural Network (201) can be trained to identify a diagnosis of the condition, a prediction of time to an occurrence of the condition, and/or a severity level of the condition in the predicted occurrence.

For example, the output (213) can be generated by at least one processing unit (111) in the integrated circuit device (101) executing instructions (205) having matrix operands to implement the Artificial Neural Network (201) using matrices (207) of the Artificial Neural Network (201) stored in random access memory (105) of the integrated circuit device (101).

At block 307, the edge server (245) transmits an alert from the integrated circuit device (245) to request intervention of the condition for the person (251).

For example, the random access memory (101) can store instructions of a server application (216). When a Central Processing Unit (225) of the integrated circuit device (101) and/or the edge server (245) executes the instructions of the server application (216), the server application (216) can generate the alert based on the output (213).

Optionally, the output (213) from the Artificial Neural Network (201) an include features extracted from the sensor data from the sensors (e.g., 247, 248, 249) in the local area network (243). The server application (216) communicates the extracted features to a central server (255) to predict a medical diagnosis for the person, the predict a need to request the input (211) from the edge server (245), and/or to determine a need to request intervention by persons having mobile devices (257). The mobile devices (257) can be configured to receive the information about the person (251), the condition of the person, a portion of the sensor data, and/or predictions made based on the sensor data.

Optionally, the central server (255) can transmit a request to the edge server (245). In response to the request, the edge sever (245) transmits sensor data to the central server (255) to facilitate further analysis by the central server (255) and/or by an expert, and/or to facilitate further training of the Artificial Neural Network (201).

For example, the edge server (245) can be configured to store sensor data collected in a latest time period of a predetermined length (e.g., a minute, 10 minutes, half an hour, or an hour). After the intervention, or inspection of the person (251), a preferred diagnosis, the timing of occurrence of a predicted condition, and/or the rating of the severity of the condition can be provided as input to the central server (255) to construct a training dataset. The Artificial Neural Network (201) can be further trained using a supervised machine learning technique to minimize the difference between the output of the Artificial Neural Network (201) and the diagnosis, measurement, rating provided by a human expert or medical practitioner.

For example, the sensor data collected in the latest time period can be transmitted to the central server (245) in response to the alert for intervention and/or in response to a request from the central server (255).

For example, the edge server (245) can be implemented in a router of the local area network (243) that connects the medical devices and sensors (e.g., 247, 248, 249). Thus, the computation workload can be offloaded from the central server (255) to the respective edge servers (e.g., 245); and the transmission of the sensor data can be limited within respective local area networks, before a potentially dangerous or usual condition is detected for intervention.

The present disclosure includes methods and apparatuses which perform the methods described above, including data processing systems which perform these methods, and computer readable media containing instructions which when executed on data processing systems cause the systems to perform these methods.

A typical data processing system may include an interconnect (e.g., bus and system core logic), which interconnects a microprocessor(s) and memory. The microprocessor is typically coupled to cache memory.

The inter-connect interconnects the microprocessor(s) and the memory together and also interconnects them to input/output (I/O) device(s) via I/O controller(s). I/O devices may include a display device and/or peripheral devices, such as mice, keyboards, modems, network interfaces, printers, scanners, video cameras and other devices known in the art. In one embodiment, when the data processing system is a server system, some of the I/O devices, such as printers, scanners, mice, and/or keyboards, are optional.

The inter-connect can include one or more buses connected to one another through various bridges, controllers and/or adapters. In one embodiment the I/O controllers include a USB (Universal Serial Bus) adapter for controlling USB peripherals, and/or an IEEE-1394 bus adapter for controlling IEEE-1394 peripherals.

The memory may include one or more of: ROM (Read Only Memory), volatile RAM (Random Access Memory), and non-volatile memory, such as hard drive, flash memory, etc.

Volatile RAM is typically implemented as dynamic RAM (DRAM) which requires power continually in order to refresh or maintain the data in the memory. Non-volatile memory is typically a magnetic hard drive, a magnetic optical drive, an optical drive (e.g., a DVD RAM), or other type of memory system which maintains data even after power is removed from the system. The non-volatile memory may also be a random access memory.

The non-volatile memory can be a local device coupled directly to the rest of the components in the data processing system. A non-volatile memory that is remote from the system, such as a network storage device coupled to the data processing system through a network interface such as a modem or Ethernet interface, can also be used.

In the present disclosure, some functions and operations are described as being performed by or caused by software code to simplify description. However, such expressions are also used to specify that the functions result from execution of the code/instructions by a processor, such as a microprocessor.

Alternatively, or in combination, the functions and operations as described here can be implemented using special purpose circuitry, with or without software instructions, such as using Application-Specific Integrated Circuit (ASIC) or Field-Programmable Gate Array (FPGA). Embodiments can be implemented using hardwired circuitry without software instructions, or in combination with software instructions. Thus, the techniques are limited neither to any specific combination of hardware circuitry and software, nor to any particular source for the instructions executed by the data processing system.

While one embodiment can be implemented in fully functioning computers and computer systems, various embodiments are capable of being distributed as a computing product in a variety of forms and are capable of being applied regardless of the particular type of machine or computer-readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

Routines executed to implement the embodiments may be implemented as part of an operating system or a specific application, component, program, object, module or sequence of instructions referred to as "computer programs." The computer programs typically include one or more instructions set at various times in various memory and storage devices in a computer, and that, when read and executed by one or more processors in a computer, cause the computer to perform operations necessary to execute elements involving the various aspects.

A machine readable medium can be used to store software and data which when executed by a data processing system causes the system to perform various methods. The executable software and data may be stored in various places including for example ROM, volatile RAM, non-volatile memory and/or cache. Portions of this software and/or data may be stored in any one of these storage devices. Further, the data and instructions can be obtained from centralized servers or peer to peer networks. Different portions of the data and instructions can be obtained from different centralized servers and/or peer to peer networks at different times and in different communication sessions or in a same communication session. The data and instructions can be obtained in entirety prior to the execution of the applications. Alternatively, portions of the data and instructions can be obtained dynamically, just in time, when needed for execution. Thus, it is not required that the data and instructions be on a machine readable medium in entirety at a particular instance of time.

Examples of computer-readable media include but are not limited to non-transitory, recordable and non-recordable type media such as volatile and non-volatile memory devices, Read Only Memory (ROM), Random Access Memory (RAM), flash memory devices, floppy and other removable disks, magnetic disk storage media, optical storage media (e.g., Compact Disk Read-Only Memory (CD ROM), Digital Versatile Disks (DVDs), etc.), among others. The computer-readable media may store the instructions.

The instructions may also be embodied in digital and analog communication links for electrical, optical, acoustical or other forms of propagated signals, such as carrier waves, infrared signals, digital signals, etc. However, propagated signals, such as carrier waves, infrared signals, digital signals, etc. are not tangible machine readable medium and are not configured to store instructions.

In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

In various embodiments, hardwired circuitry may be used in combination with software instructions to implement the techniques. Thus, the techniques are neither limited to any specific combination of hardware circuitry and software nor to any particular source for the instructions executed by the data processing system.

The above description and drawings are illustrative and are not to be construed as limiting. Numerous specific details are described to provide a thorough understanding. However, in certain instances, well known or conventional details are not described in order to avoid obscuring the description. References to one or an embodiment in the present disclosure are not necessarily references to the same embodiment; and, such references mean at least one.

In the foregoing specification, the disclosure has been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

What is claimed is:

1. A method, comprising:
    storing, in random access memory of an integrated circuit device having at least one processing unit configured to execute instructions having matrix operands, a model of an Artificial Neural Network;
    receiving, in the integrated circuit device and from a computer network, sensor data of a person;
    generating, in the integrated circuit device and by the at least one processing unit executing instructions included in the model of the Artificial Neural Network, an output of the Artificial Neural Network, based on the model stored in the integrated circuit device and the sensor data of the person, wherein the output identifies a condition of the person;
    transmitting an alert from the integrated circuit device to request assistance; and
    executing, by the at least one processing unit configured in the integrated circuit device, the instructions included in the model of the Artificial Neural Network to implement the Artificial Neural Network using matrices of the Artificial Neural Network stored in the random access memory configured in the integrated circuit device;
    wherein the integrated circuit device has a Deep Learning Accelerator with the at least one processing unit, a control unit and local memory; the at least one processing unit includes at least a matrix-matrix unit configured to execute an instruction having two matrix operands; the at least one matrix-matrix unit includes a plurality of matrix-vector units configured to operate in parallel; each matrix-vector units, from the plurality of matrix-vector units, includes a plurality of vector-vector units configured to operate in parallel; and each vector-vector units, from the plurality of vector-vector units, includes a plurality of multiply-accumulate units configured to operate in parallel.

2. The method of claim 1, wherein the output further identifies a diagnosis of the condition.

3. The method of claim 2, wherein the output further identifies a prediction of time to an occurrence of the condition.

4. The method of claim 3, wherein the output further identifies a severity level of the condition in the occurrence.

5. The method of claim 3, further comprising:
extracting features from the sensor data; and
transmitting the features to a central server to predict a medical diagnosis for the person.

6. The method of claim 5, further comprising:
receiving a request from the central server; and
transmitting the sensor data to the central server.

7. The method of claim 3, further comprising:
storing sensor data collected in a latest time period of a predetermined length; and
transmitting the sensor data collected in the latest time period to a central server, wherein the central server is configured to train the Artificial Neural Network based on input provided by a human and a supervised machine learning technique.

8. The method of claim 7, wherein the sensor data collected in the latest time period is transmitted to the central server in response to the alert.

9. The method of claim 7, further comprising:
receiving a request from the central server, wherein the request causes transmission of the sensor data collected in the latest time period to the central server.

10. The method of claim 1, wherein the random access memory further stores instructions of a server application configured to generate the alert based on the output; and the integrated circuit device further includes a Central Processing Unit configured to execute the instructions.

11. The method of claim 10, further comprising:
communicating, within a local area network, with sensors to receive the sensor data.

12. The method of claim 11, wherein the sensors include a vital sign monitor and a digital camera.

13. An apparatus, comprising:
a communication device configured to receive sensor data of a person;
a Central Processing Unit;
at least one processing unit configured to execute instructions having matrix operands;
random access memory configured to store:
matrices of an Artificial Neural Network;
instructions executable by the at least one processing unit to implement the Artificial Neural Network, wherein the instructions are included in the model of the Artificial Neural Network to implement the Artificial Neural Network using matrices of the Artificial Neural Network stored in the random access memory configured in an integrated circuit device; and
a server application programmed for execution by the Central Processing Unit to provide, based on an output of the Artificial Neural Network, an alert to request intervention of a condition of the person identified in the output; and
an integrated circuit package enclosing the at least one processing unit and the random access memory;
wherein the integrated circuit device has a Deep Learning Accelerator with the at least one processing unit, a control unit and local memory; the at least one processing unit includes at least a matrix-matrix unit configured to execute an instruction having two matrix operands; the at least one matrix-matrix unit includes a plurality of matrix-vector units configured to operate in parallel; each matrix-vector units, from the plurality of matrix-vector units, includes a plurality of vector-vector units configured to operate in parallel; and each vector-vector units, from the plurality of vector-vector units, includes a plurality of multiply-accumulate units configured to operate in parallel.

14. The apparatus of claim 13, wherein the integrated circuit package further encloses the Central Processing Unit.

15. The apparatus of claim 14, further comprising:
sensors configured to monitor the person and generate the sensor data in a local area network that is connected to the communication device.

16. The apparatus of claim 15, further comprising:
a router of the local area network;
wherein the integrated circuit package is configured within the router; and
wherein the alert is transmitted via a central server, a telecommunications network, a cellular communications network, or Internet.

17. A system, comprising:
a central server;
a plurality of edge servers in communication with the central server, wherein each respective edge server in the plurality of edge servers includes:
a communication device configured to receive sensor data of a person;
a Central Processing Unit having at least one Arithmetic-Logic Unit (ALU);
a Deep Learning Accelerator having at least one processing unit that includes at least a matrix-matrix unit configured to operate on two matrix operands of an instruction executable in the Deep Learning Accelerator, the at least one matrix-matrix unit includes a plurality of matrix-vector units configured to operate in parallel; each matrix-vector units, from the plurality of matrix-vector units, includes a plurality of vector-vector units configured to operate in parallel; and each vector-vector units, from the plurality of vector-vector units, includes a plurality of multiply-accumulate units configured to operate in parallel; and
random access memory configured to store:
matrices of an Artificial Neural Network;
instructions executable by the Deep Learning Accelerator to generate, according to the sensor data as input to the Artificial Neural Network, an output identifying a condition of the person, wherein the instructions are included in the model of the Artificial Neural Network to implement the Artificial Neural Network using matrices of the Artificial Neural Network stored in the random access memory configured in an integrated circuit device; and
a server application executable by the Central Processing Unit to provide an alert to the central server, the central server configured to request intervention of the condition for the person in response to the alert.

18. The system of claim 17, further comprising:
an integrated circuit package configured to enclose at least the random access memory and the Deep Learning Accelerator.

* * * * *